(12) United States Patent
Shpigelmacher et al.

(10) Patent No.: US 12,070,281 B2
(45) Date of Patent: Aug. 27, 2024

(54) METHODS AND SYSTEMS TO CONTROL PARTICLES AND IMPLANTABLE DEVICES

(71) Applicant: BIONAUT LABS LTD., Herzliya (IL)

(72) Inventors: Michael Shpigelmacher, Los Angeles, CA (US); Alex Kiselyov, San Diego, CA (US); Leslie Field, Portola Valley, CA (US); Mateusz Bryning, San Jose, CA (US); Phillip Barth, Portola Valley, CA (US)

(73) Assignee: BIONAUT LABS LTD. (IL)

( * ) Notice: Subject to any disclaimer, the term of this patent is extended or adjusted under 35 U.S.C. 154(b) by 1072 days.

(21) Appl. No.: 16/620,748

(22) PCT Filed: May 3, 2018

(86) PCT No.: PCT/US2018/030960
§ 371 (c)(1),
(2) Date: Dec. 9, 2019

(87) PCT Pub. No.: WO2019/005293
PCT Pub. Date: Jan. 3, 2019

(65) Prior Publication Data
US 2020/0196995 A1    Jun. 25, 2020

Related U.S. Application Data

(60) Provisional application No. 62/524,650, filed on Jun. 26, 2017.

(51) Int. Cl.
*A61M 37/00* (2006.01)
*A61B 5/00* (2006.01)
(Continued)

(52) U.S. Cl.
CPC ............ *A61B 34/30* (2016.02); *A61B 5/0002* (2013.01); *A61B 10/02* (2013.01);
(Continued)

(58) Field of Classification Search
CPC ........... A61B 2017/00345; A61B 2017/00411; A61B 2562/028; A61B 2562/162; A61B 34/30; A61B 5/0002
See application file for complete search history.

(56) References Cited

U.S. PATENT DOCUMENTS

2002/0194942 A1    12/2002  Jensen et al.
2003/0181788 A1 *   9/2003  Yokoi ................... A61B 1/041
                                                     600/117
(Continued)

FOREIGN PATENT DOCUMENTS

JP      2003/275170      9/2003
WO      WO-2009/145405   12/2009

OTHER PUBLICATIONS

Extended European Search Report dated Feb. 15, 2021 in respect of corresponding EP Application No. 18822994.2.
(Continued)

*Primary Examiner* — Jenna Zhang
(74) *Attorney, Agent, or Firm* — Mark S. Cohen; PEARL COHEN ZEDEK LATZER BARATZ LLP

(57) ABSTRACT

A platform and methods of use, for providing active, predetermined, fully controlled, precise delivery of nano- or micro-particles in biological tissue. The platform comprises the following modules: (A) one or more nano- or micro-particles comprising embedded logic and various MEM components; (B) a delivery and retraction module, configured to deliver and retract the particles; (C) an external signal generator; (D) an imaging module, configured to monitor said particles; and (E) an integration module configured to receive inputs from other modules and provide output control commands to other modules. The modules are configured to interact/communicate with each other and are internally controlled, externally controlled or both.

9 Claims, 20 Drawing Sheets

(51) Int. Cl.
*A61B 10/02* (2006.01)
*A61B 34/30* (2016.01)
*A61M 5/142* (2006.01)
*A61B 17/00* (2006.01)
*A61N 5/10* (2006.01)

(52) U.S. Cl.
CPC .... *A61M 5/14276* (2013.01); *A61M 37/0069* (2013.01); *A61B 2010/0208* (2013.01); *A61B 2017/00345* (2013.01); *A61B 2017/00411* (2013.01); *A61B 2034/303* (2016.02); *A61B 2560/0214* (2013.01); *A61B 2562/028* (2013.01); *A61M 2205/0244* (2013.01); *A61M 2205/0288* (2013.01); *A61M 2205/0294* (2013.01); *A61N 5/1007* (2013.01)

(56) References Cited

U.S. PATENT DOCUMENTS

| | | |
|---|---|---|
| 2004/0257403 A1 | 12/2004 | Silverbrook |
| 2006/0063964 A1 | 3/2006 | Massen |
| 2008/0033569 A1* | 2/2008 | Ferren ............... A61B 17/295 |
| | | 623/23.7 |
| 2009/0227988 A1 | 9/2009 | Wood, Jr. et al. |
| 2011/0200948 A1 | 8/2011 | Yu |
| 2011/0254107 A1 | 10/2011 | Bulovic et al. |
| 2011/0270434 A1 | 11/2011 | Fischer et al. |
| 2012/0069209 A1 | 3/2012 | Gudlavalleti et al. |
| 2012/0206134 A1 | 8/2012 | Fischer et al. |
| 2013/0002244 A1 | 1/2013 | Quevy |
| 2013/0190752 A1* | 7/2013 | Zurn ............... A61B 18/245 |
| | | 606/41 |
| 2014/0072632 A1 | 3/2014 | DeSimone et al. |
| 2015/0374395 A1 | 12/2015 | Creighton |

OTHER PUBLICATIONS

International Search Report for PCT Application No. PCT/US2018/030960 dated Jul. 27, 2018.

Robert A. Freitas, "Comprehensive Nanorobotic Control of Human Morbidity and Aging" The Future of Aging, May 25, 2010, pp. 685-805.

Office Action dated Jan. 18, 2022 in respect of JP Patent Application No. 2019-271233 (with English translation thereof).

Office Action dated Sep. 6, 2022 in respect of JP Patent Application No. 2019-571233 (with English translation thereof).

* cited by examiner

METHODS AND SYSTEMS TO CONTROL PARTICLES AND IMPLANTABLE DEVICES

CROSS-REFERENCE TO RELATED APPLICATIONS

This application is a U.S. national stage application under 37 U.S.C. 371 of PCT International Application PCT/US2018/030960, filed May 3, 2018, which claims benefit of U.S. Provisional Patent Application Ser. No. 62/524,650, filed Jun. 26, 2017, the priority date of which is hereby claimed, the contents of each of which is hereby incorporated by reference in its entirety.

BACKGROUND OF THE INVENTION

For a variety of medical applications, it may be desirable to remotely control or power miniature objects on the nano-to-mm scale (e.g., particles or implantable devices) inside biological tissue. Such objects may be used to complete specific tasks for a medical purpose, including active and directed motion, localized mechanical manipulation, controlled chemical payload release, sensor activation, data transmission, etc. Thus, methods to remotely communicate with miniature objects, such as particles which have an embedded magnetic component (e.g., Magnetically Actuated Propellers (MAPs) described in U.S. Pat. No. 8,768,501, which is incorporated herein by reference in its entirety), designed to move in an external rotating electromagnetic field using electromagnetic waves or ultrasound, as well as to remotely power such objects using electromagnetic waves or ultrasound.

These miniature objects generally contain at least 3 main microelectromechanical (MEM) components, namely: (1) an integrated circuit (IC) containing the embedded logic for the object's operation; (2) a power source, which could be internal (such as a miniature battery) or external (via remote power transfer) powering the IC; and (3) control nodes (e.g., a mechanical manipulator, a molecular sensor, or a remote communication transmitter/receiver) connected to the IC inputs and outputs.

Several methods for powering miniaturized medical devices are known (e.g., internal battery, RF-based wireless power transfer, harvesting of biological fuel material available in the body). See, e.g., Basar, et al., *International Journal of Antennas and Propagation*, Volume 2012 (2012); and RF power harvesting: a review on designing methodologies and applications, Tran et al., *Micro and Nano Systems Letters* (2017) 5:14. However, these methods suffer from various limitations, such as:

Internal batteries are greatly limited in storage capacity, especially at the sub-mm scale.

The requirement of clinical safety greatly limits choice of materials in battery design.

The efficiency of harvesting biologically available materials in the body as fuels is greatly limited.

Also, given the approximate scale similarity between RF antenna size and wavelength, constructing an RF receiver antenna at the sub-mm scale requires using the GHz-THz wavelength range, where RF radiation has limited penetration in human tissue. This greatly limits wireless RF power transfer at the sub-mm size scale. Similarly, RF communication to particles and implantable devices in the human body is challenging to implement on the sub-mm scale, both for the downlink (communication to a particle/implantable device) and the uplink (transmission from a particle/implantable device).

SUMMARY OF THE INVENTION

In one aspect, provided herein are microelectromechanical (MEM) devices, the MEM devices comprise:
an actuator;
a responsive element;
a sensor; and
an electronic circuit;
wherein:
said actuator controls and operates said responsive element;
said electronic circuit controls said actuator; and
said sensor receives signals transmitted by a remote unit.

In another aspect, provided herein are platforms comprising the following modules:
one or more nano- or micro-particles comprising embedded logic and various MEM components;
a delivery and/or retraction module, configured to deliver and/or retract the particles;
an external signal generator;
an imaging module, configured to monitor said particles; and
an integration module configured to receive inputs from and to provide output control commands to other modules;
wherein:
said modules are configured to interact/communicate with each other; and
said modules are internally controlled, externally controlled or both;
and wherein said platform provides active, pre-determined, fully controlled, precise delivery of said particles in vitro, in vivo, and/or in a patient.

In some embodiments, a nano- or micro-particle is a MEM device described herein.

In another aspect, provided herein are systems, the systems comprise: a platform described herein and a remote unit comprising a transmitter, a receiver or a combination thereof; wherein said remote unit is configured to communicate with said platform.

In another aspect, provided herein are methods for communicating with a MEM device, the methods comprise:
providing a MEM device comprising:
at least one responsive element;
at least one sensor; and
an electronic circuit;
wherein:
said electronic circuit is configured to control said responsive element; and
said sensor is configured to receive signals transmitted by a remote unit;
transmitting and/or receiving a signal to/from said device, wherein said signal comprises one or more of:
a magnetic signal, an electric signal or a combination thereof;
an acoustic or ultrasound signal;
an electromagnetic radiation signal; or
an optical signal.

In another aspect, provided herein are methods of treating a subject, the methods comprise:
providing a MEM device comprising:
at least one responsive element;
at least one sensor; and
an electronic circuit;

wherein:
said electronic circuit is configured to control said responsive element; and
said sensor is configured to receive signals transmitted by a remote unit;
inserting said device into said subject;
transmitting and/or receiving a signal to/from said device, wherein said signal comprises one or more of:
a magnetic signal, an electric signal or a combination thereof;
an acoustic or ultrasound signal;
an electromagnetic radiation signal; or
an optical signal;
such that said signal is used for a treatment operation on said subject.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
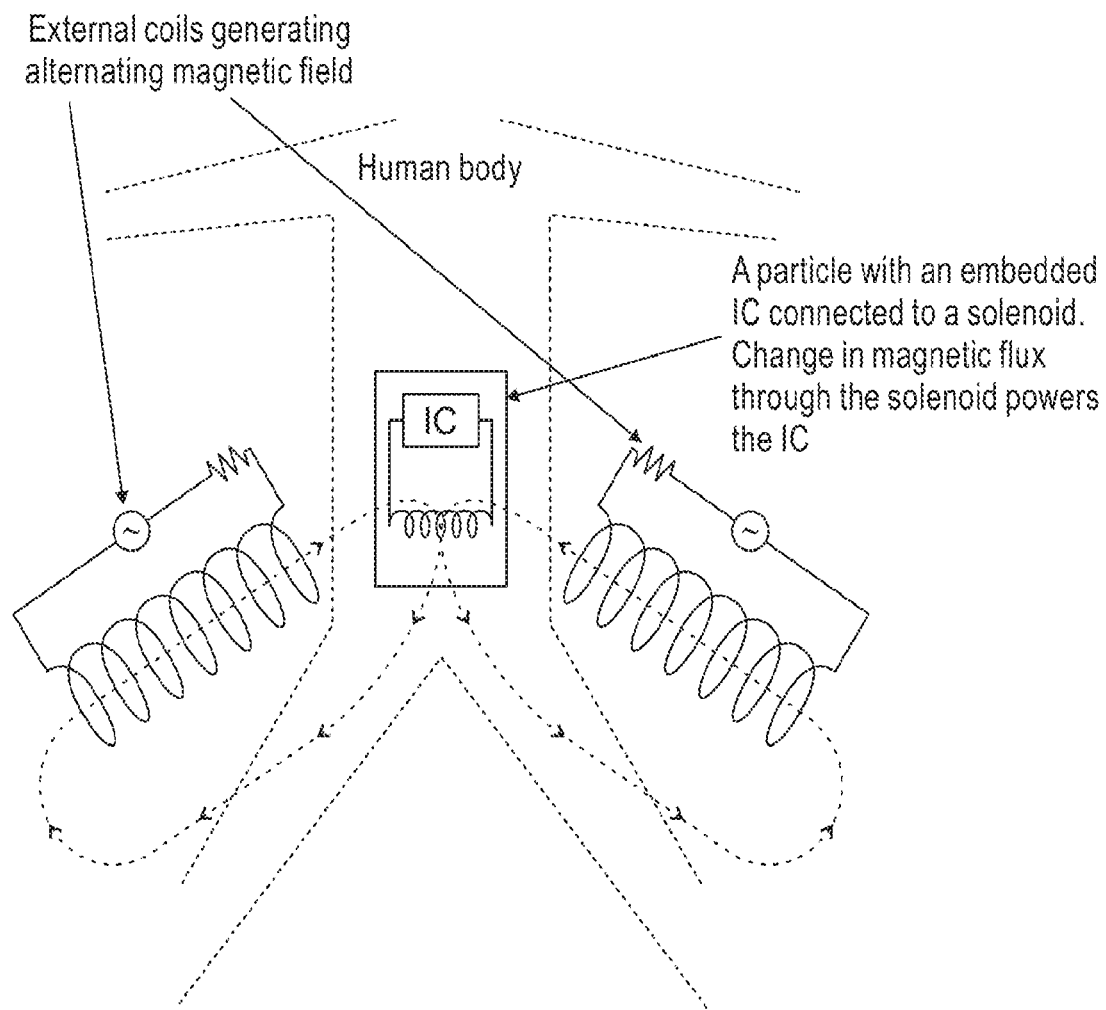
FIG. 1 schematically shows a particle in a human body. The particle comprises an embedded integrated circuit (IC) connected to a solenoid. Change in magnetic flux through the solenoid powers the IC.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one aspect, provided herein are microelectromechanical (MEM) devices, the MEM devices comprise:
an actuator;
a responsive element;
a sensor; and
an electronic circuit;
wherein:
said actuator controls and operates said responsive element;
said electronic circuit controls said actuator; and
said sensor receives signals transmitted by a remote unit.

In another aspect, provided herein are platforms comprising the following modules:
one or more nano- or micro-particles comprising embedded logic and various MEM components;
a delivery and/or retraction module, configured to deliver and/or retract the particles;
an external signal generator;
an imaging module, configured to monitor said particles; and
an integration module configured to receive inputs from and to provide output control commands to other modules;
wherein:
said modules are configured to interact/communicate with each other; and
said modules are internally controlled, externally controlled or both;
and wherein said platform provides active, pre-determined, fully controlled, precise delivery of said particles in vitro, in vivo, and/or in a patient.

In some embodiments, a nano- or micro-particle is a MEM device described herein.

In another aspect, provided herein are systems, the systems comprise: a platform described herein and a remote unit comprising a transmitter, a receiver or a combination thereof; wherein said remote unit is configured to communicate with said platform.

In another aspect, provided herein are methods for communicating with a MEM device, the methods comprise:
providing a MEM device comprising:
at least one responsive element;
at least one sensor; and
an electronic circuit;
wherein:
said electronic circuit is configured to control said responsive element; and
said sensor is configured to receive signals transmitted by a remote unit;
transmitting and/or receiving a signal to/from said device, wherein said signal comprises one or more of:
a magnetic signal, an electric signal or a combination thereof;
an acoustic or ultrasound signal;
an electromagnetic radiation signal; or
an optical signal.

In another aspect, provided herein are methods of treating a subject, the methods comprise:
providing a MEM device comprising:
at least one responsive element;
at least one sensor; and
an electronic circuit;
wherein:
said electronic circuit is configured to control said responsive element; and
said sensor is configured to receive signals transmitted by a remote unit;
inserting said device into said subject;
transmitting and/or receiving a signal to/from said device, wherein said signal comprises one or more of:
a magnetic signal, an electric signal or a combination thereof;
an acoustic or ultrasound signal;
an electromagnetic radiation signal; or
an optical signal;
such that said signal is used for a treatment operation on said subject.

The platforms described herein may be used for active, pre-determined and precise delivery of nano- and micro-particles for carrying and controlling release of cargo, diagnostics, or a combination thereof and/or localized manipulation of particle environment, in vitro, ex vivo, in vivo and in patients. These platforms comprise interacting modules with internal and external diagnostics, and control and communication capabilities. The modules include:

A nano- or micro-particle or multiple such particles that respond to external stimuli generated by an external signal generator in a diverse fashion, for example to harvest power to operate internal MEM components and integrated circuits, to actively move through its environment, to carry and release cargo, for localized mechanical manipulation of actuators or of its environment, for sensory activity, to communicate, to collect cargo from its environment, to retract particles from its operating environment, for chemical, physical or thermal manipulation of particle or its environment.

An external signal generator, as exemplified but not limited to electromagnetic, ultrasound, piezoelectric, RF, HF, optical or alternative signal generators.

An imaging module to monitor the particles, as exemplified but not limited to acoustic-, radio-frequency —, electromagnetic-, optics-based devices.

A delivery and/or retraction module to deliver and/or collect the particles.

An integration module comprised of respective hardware and software to secure active, pre-determined delivery of particles to specified locations in vitro, ex vivo, in vivo, or in patients, and for accurate control of their operation.

Three-dimensional components of the particles, devices, systems and platforms described herein can be manufactured using a variety of techniques known in the art, including FIB (Focused Ion Beam). Planar components of the particles, devices, systems and platforms described herein can be manufactured using MEM IC fabrication techniques known in the art.

Examples of methods to manufacture three-dimensional (3-D) components include FIB (Focused Ion Beam), 3-D printing in metals or polymers or other materials, laser or chemical etching, lost wax casting, molding, photolithography, laser or mechanical machining, as well as other MEM fabrication methods. For helical twisted components specifically, other methods may include laser etching or machining (e.g., laser machining of small diameter nitinol tubing), micromilling, physical twisting of wires or other flexible elements, mechanical micromachining, or the use of self-rolled micro-springs made from strained nanomembranes (see Huant et al., *Nanoscale* (2014) 6(16):9428-35).

Planar components can be manufactured using MEM IC fabrication techniques known in the art.

Figure 7:
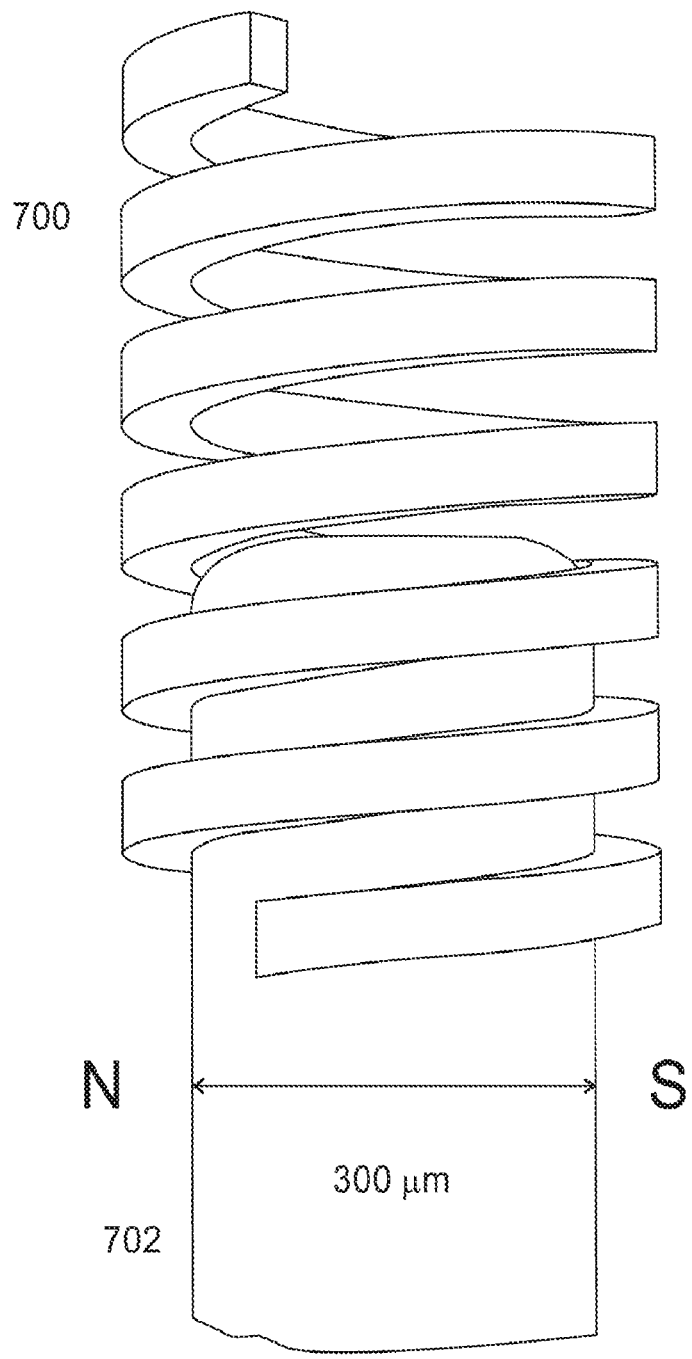
FIG. 7 schematically shows a helical coil component 700 manufactured separately from an embedded magnetic pellet 702. The pellet is inserted into the coil. Alternatively, a helical coil or multiple helical coils could be structural parts of a particle (e.g., etched, cut on the surface of a cylinder, conus, rod) that embeds magnetic pellet 702.
Figure 8:
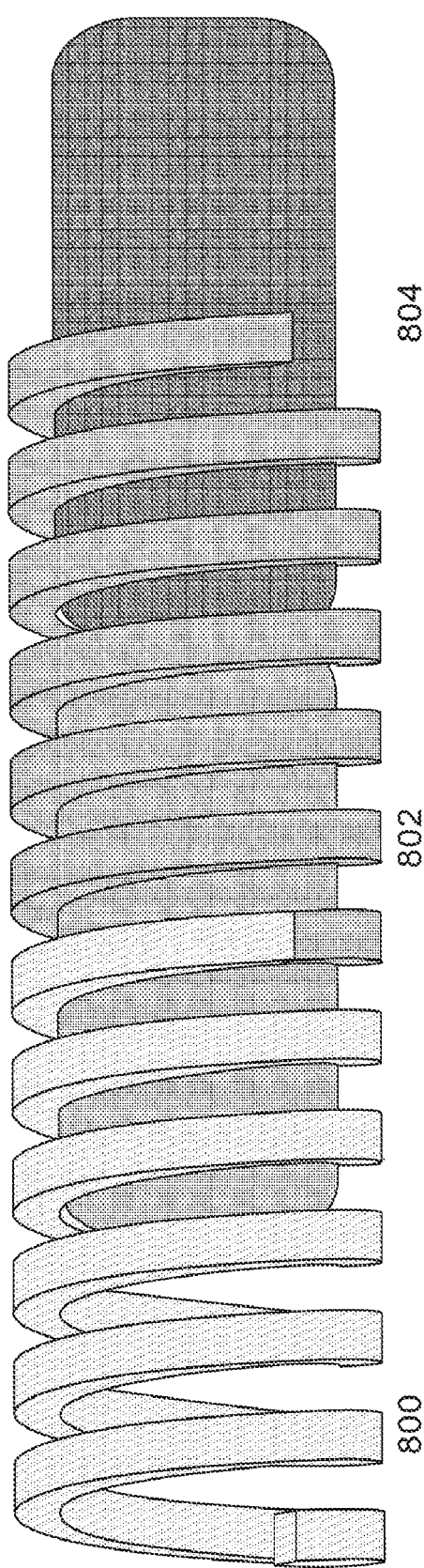
FIG. 8 schematically shows a helical coil 800 with multiple modules (modules 802 and 804 are exemplified). The modules can be inserted into the coil or a single solid particle that contains helical topology one after the other.
Figure 9:
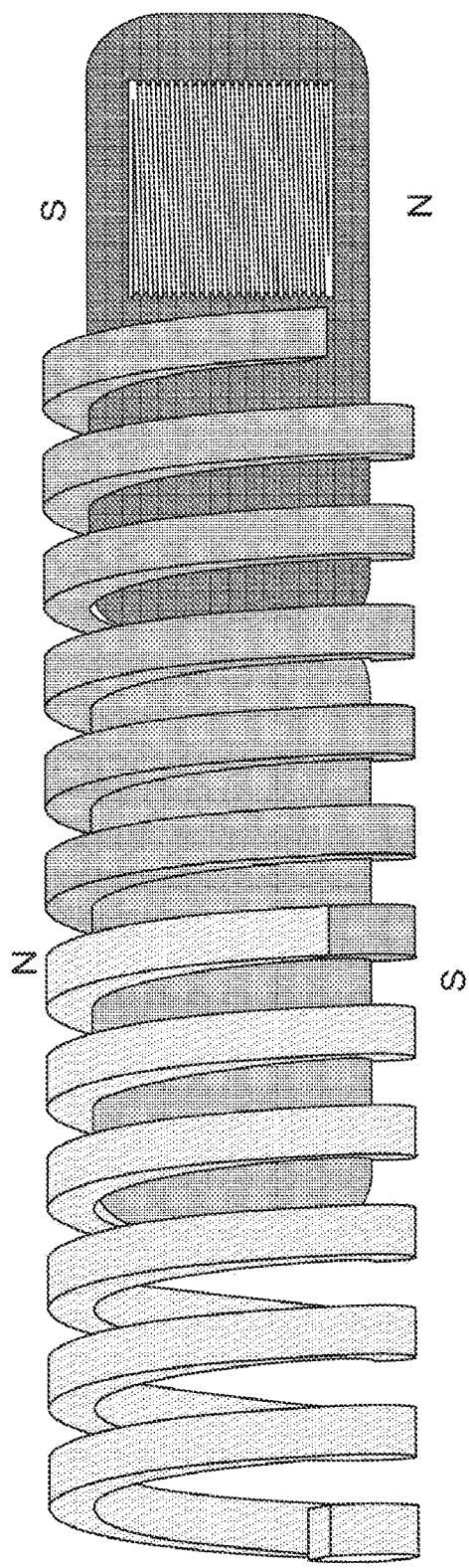
FIG. 9 schematically shows a helical coil 900 with multiple modules (modules 902 and 904 are exemplified), the figure schematically shows coil components that can be added to increase coil length and improve mobility One of the modules has a power harvesting coil that is either orthogonal (A) or parallel (B) to the helical coil axis.
Figure 9:
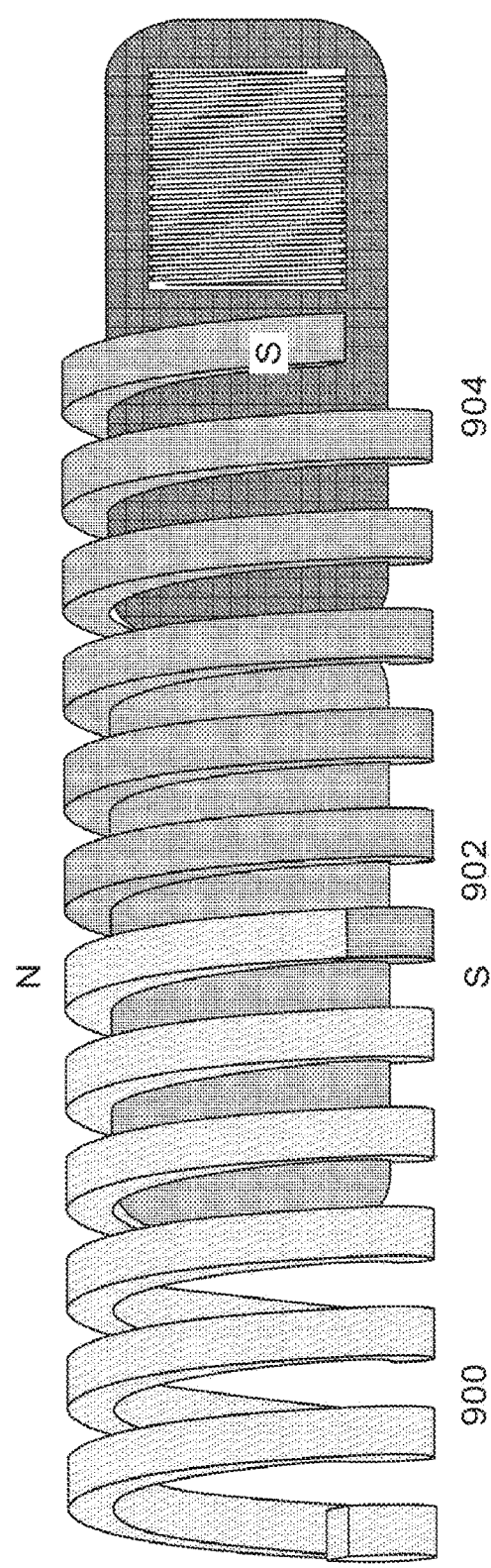

Separate components can be manufactured in isolation, and later joined. For example, as illustrated in FIG. 7, helical coil component 700 is manufactured separately from an embedded magnetic "pellet" 702, and the pellet 702 is inserted into the coil 700. Using this method, multiple modules can be inserted into the coil one after the other, as illustrated in FIG. 8. New coil components can be added to increase coil length and improve mobility, as illustrated in FIGS. 9A and 9B.

The external signal generator module is aimed at securing accurate remote control of particles, including control of particle motion, remote energy transfer to particles to provide power for their operation and data communication with them. The external signal generator may contain one or more signal channels, each channel uses a different physical signaling mechanism, including HF, RF, ultrasound, optical, radiation, and electromagnetic signals.

In some embodiments, the external signal generator includes a channel generating an electromagnetic signal. The electromagnetic field generated by a specific signal channel may have specific characteristics including orientation, gradient, topology, field strength, field homogeneity per unit of volume. The electromagnetic field could be ascertained via one or a series of Helmholtz, Maxwell coils, Halbach arrays of permanent magnets, relevant permanent magnets alternatives or a combination thereof. Furthermore, the electromagnetic field may be rotating, pulsating, fixed, contain a gradient or a combination thereof.

In some embodiments, the electromagnetic signal may exert a force to move the particles, including a rotational force using a rotating magnetic field, a push/pull force using a magnetic field gradient, or other suitable electromagnetic force generating mechanisms.

In some embodiments, the signal generator includes a signal channel to transfer energy remotely to particles using RF, HP, ultrasound or other suitable signal types.

In some embodiments, the signal generator transfers other operational commands (downlink communication) to particles via the same signal channel used to remotely transfer energy, or via other dedicated communication channels, including electromagnetic, ultrasound, RF, optical, and HP. Energy transferred to particles is harvested by them and used to provide power for their operation and execution of the operational commands.

In some embodiments, the electromagnetic signal facilitates accurate location of a particle by generating a set of distinct electromagnetic features measurable by a particle across operation space and serving as coordinates in operational space. For example, the features may include a magnetic field gradient as a function of location.

In some embodiments, the external signal generator may receive communication messages (uplink communication) from particles via the same signal channel used for other purposes, such as remote energy transfer or downlink communication. In other embodiments, the external signal generator may receive communication messages via a separate dedicated channel, including but not limited to electromagnetic, ultrasound, RF, optical or HP.

The imaging module is aimed at visualization of particles in vitro, ex vivo, in vivo or in a human patient. The imaging module may include RF, ultrasound, piezoelectric, electromagnetic, optical or other suitable elements or a combination thereof. In some embodiments, the imaging module comprises ultrasound-computational tomography or any relevant manifestations thereof. In some embodiments, the imaging module is a standalone ultrasound device. In some embodiments, the imaging module comprises multiple ultrasound sensors with integrated tracking logic implemented by the integration module and that is specifically configures to visualize nano- or micro-particles.

The particle module is aimed at accurate delivery of a diagnostic, therapeutic cargo or therapy, a combination thereof, or other localized manipulation of a particle or its environment at a specific location and/or a specific time. The particle module may include particles that respond to external stimuli to perform a variety of localized operations. In some embodiments, the particles carry a specific therapeutic cargo. In other embodiments, the particles carry a combination of several cargos. In some embodiments, the particles carry diagnostic agents, therapeutic agents or a combination thereof.

The stimuli may include signals or remote-control commands transmitted from the external signal generator, signals or commands communicated by other particles, and/or localized chemical or physical stimuli as sensed by the particle via embedded sensors.

In some embodiments, the localized operations comprise generating local thermal or radiation exposure, for example, thermal neutron particle-based and/or alpha particle-based radiation. In some embodiments, the localized operations comprise manipulation of MEM components connected to or embedded in the particles. In some embodiments, the localized operations comprise mechanical manipulation of the particle environment. In some embodiments, the localized operations comprise moving a particle or its components in relation to the environment. In some embodiments, the localized operations comprise release of particle cargo.

In some embodiments, the localized operation may include gathering sensory data, such as medical diagnostics, chemical sensors, biochemical sensors, flow sensors, rheology sensors, temperature or magnetic field gradients. In some embodiments, the localized operation may include communication of data from a particle to the external signal generator or other particles. In some embodiments, the localized operation may include gathering samples from the particle environment, such as a biopsy.

In some embodiments, the particle is configured for active transport when subject to the external stimuli. In some embodiments, the particle is configured to deliver cargo as a whole, in a gradient or in a stop-and-go fashion.

In some embodiments, the particle comprises specific features aimed at enhanced imaging and/or detection via external devices. For example, such features may include a specialized surface, topology, materials, or a combination thereof. Specialized image enhancing features may include microbubbles, microcavities, microrattles, localized measurement of magnetic field gradients, or communication antennae.

In some embodiments, the particle comprises compartments to accommodate i) tissue penetration; ii) mobility, including complex 3D as well as stop-and-go motion; iii) therapeutic effect, including loading and unloading of specific cargo or a combination of several agents; iv) sample collection from its environment v) uplink and/or downlink communication; vi) sensory; vii) power harvesting; viii) logic control and computation, and/or ix) retraction of particles from operating volume.

The delivery and/or retraction module is aimed at controlled delivery and/or collection of a nano- or micro-particle to and from specific locations (in vitro, ex vivo, in vivo in a mammal, or in vivo in a human patient.) prior to and after control with external stimuli, as well as upon completion of particle operation. In some embodiments, the delivery and retraction module comprises one or more structural elements to deliver and collect or retract a particle or series of particles. The delivery and retraction module may be configured to secure single or multiple insertions for in vitro, ex vivo, in vivo, or patient applications.

In some embodiments, the delivery and retraction module comprises an attachment element selected from: magnetic or magnetizable needle, pneumatic element, cutting element (e.g., microscalpel or microchisel), expendable magnetic element, magnetic surface, electromagnetic element, ultrasonic element, deployable mesh, deployable micro-net, suction element or a combination thereof. In some embodiments, the delivery and retraction module comprises a magnetic or magnetizable needle configured to inject and collect a particle or series of particles. In some embodiments, the magnetic or magnetizable needle is configured to accommodate standalone particles. In other embodiments, the magnetic or magnetizable needle is configured to accommodate particles in a matrix to secure precise delivery. In some embodiments, the magnetic or magnetizable needle is kept in the injection matrix in vitro, ex vivo, in vivo or in a patient for the duration of treatment. In other embodiments, the magnetic or magnetizable needle is retracted and reintroduced for particle collection.

In other embodiments, the delivery and retraction module is configured to deliver a particle or series of particles using electromagnetic, ultrasound or pneumatics-based devices. In other embodiments, the delivery and retraction module is configured to collect a particle or series of particles using deployable mesh, micronet or suction. In other embodiments, the delivery and retraction module is configured to collect a particle or series of particles as part of a microbiopsy using a combination of a suction element, a guiding catheter and a cutting element, as exemplified by a microchisel or microscalpel.

In some embodiments, the internal logic in a particle or device is incorporated in an embedded memory component, and the IC and other onboard components are powered without ongoing remote power transfer. For that purpose, a localized energy storage device can be used, such as a micro super capacitor, as described in *"Interdigitated MEMS Supercapacitor for Powering Heart Pacemaker" Hafzaliza et al., ISBN* 978-953-51-2749-9, Print ISBN 978-953-51-2748-2, (November 2016). This allows autonomous or semi-autonomous operation of the particle or device.

In one aspect, provided herein are microelectromechanical (MEM) devices, the MEM devices comprise:
an actuator;
a responsive element;
a sensor; and
an electronic circuit;
wherein:
said actuator controls and operates said responsive element;
said electronic circuit controls said actuator; and
said sensor receives signals transmitted by a remote unit.

In some embodiments, the MEM device comprises a cavity. In some embodiments, the responsive element comprises a piezoelectric element, a cantilever, a membrane, a flagellum, an arm, a joint or a combination thereof. In some embodiments, the responsive element comprises an elongated element having a first end and a second end. For example, the first end is anchored and the second end is free. Alternatively, both the first and second ends are anchored. In some embodiments, the responsive element is rigid. In other embodiments, the responsive element is flexible.

In another aspect, provided herein are platforms comprising the following modules:
one or more nano- or micro-particles comprising embedded logic and various MEM components;
a delivery and/or retraction module, configured to deliver and/or retract the particles;
an external signal generator;
an imaging module, configured to monitor the particles; and
an integration module configured to receive inputs from and to provide output control commands to other modules;
wherein:
the modules are configured to interact/communicate with each other; and
the modules are internally controlled, externally controlled or both;
and wherein the platform provides active, pre-determined, fully controlled, precise delivery of the particles in vitro, ex vivo, in vivo, and/or in a patient.

In some embodiments, the particles are configured to carry and control release of single or multiple cargo, to perform diagnostics, to perform localized manipulation of the environment of said particles or a combination thereof.

In some embodiments, the external signal generator is selected from: an electromagnetic signal generator, a combination of a permanent magnet and an electromagnetic signal generator, an optical signal generator, an ultrasound signal generator or a combination thereof. In some embodiments, the electromagnetic generator is a magnetic field generator, an electric field generator or a combination thereof. In some embodiments, the electromagnetic generator operates using HBC (Human Body Communication) technology. In some embodiments, the electromagnetic field generator operates in RF, HF or UHF range (KHz-GHz range). In some embodiments, the optical signal generator operates in visible or invisible light wavelengths. In some embodiments, the ultrasound generator operates in KHz or MHz range. In some embodiments, the optical generator is an RF generator.

In some embodiments, the external signal generator provides remote control of the particles.

In some embodiments, particles respond to/communicate with an external signal generated by the signal generator in a manner selected from:
particles harvest power fully or in part from the generators for operation of internal components;
particles harvest power for particle motion;
particles release or collect cargo in response to the external signal;
particles perform sensor activity;
the external signal provides physical or chemical manipulation of the particle or of surrounding particles;
the external signal triggers/operates a responsive element based in or on the particles;
retraction of particles from a certain location;
particles transmit data to/receive data from the external generator; or
a combination thereof.

In some embodiments, the generator is an electromagnetic signal generator that exerts a force, which causes particle movement. For example, the force is a rotational force formed by a rotating magnetic field. Alternatively, the force is a push/pull force formed by magnetic field gradient. In some embodiments, the signal generator comprises a signal channel, which remotely transfers energy to the particles, and where the energy is RF, HF or ultrasound energy.

In some embodiments, the signal generator transfers additional operational commands to the particles. The additional commands may be transferred via the channel used to remotely transfer energy or via other dedicated communication channels, such as electromagnetic, ultrasound, RF, optical or HP. Examples of operational commands include: partial, complete, location and/or time-resolved release of payload, heat local tissue, transmit data, conduct diagnostic measurement, collect tissue sample, move mechanical manipulator, propel particle, ablate tissue locally, as well as other commands.

In some embodiments, energy transferred to a particle is harvested by it, and provides power for particle operation and for execution of the operational commands.

In some embodiments, the electromagnetic field generated by a specific signal channel has specific characteristics including orientation, gradient, topology, field strength or field homogeneity per unit of volume. For example, it may be desirable to generate a rotating magnetic field of 50-1500 Gauss at 1-100 Hz in a volume of 80 cm×80 cm×120 cm to allow movement of magnetic particles in a human body. It may be desirable to generate a sinusoidal magnetic field or electromagnetic field in the MHz or GHz range in a given axis to transmit data to a particle or to remotely transfer power to an embedded coil in a particle, where the particle is embedded in a unit volume as described above.

In some embodiments, the electromagnetic signal is used to accurately locate particles by generating a set of distinct electromagnetic features measurable by particles across operation space and serving as coordinates in operational space. For example, such features include magnetic field gradient as a function of location. In a non-limiting example, magnetic field gradients of up to 100 mT/M may be generated across an operational volume. The particle can sense a localized value of magnetic field gradient and communicate it back to the integration module. Assuming the values of magnetic field gradient are a one-to-one map to 3D location (i.e., gradient is unique at any point), the value of the magnetic field gradient allows accurate location of the particle.

In some embodiments, the electromagnetic field is ascertained via one or a series of Helmholtz coils, Maxwell coils, Halbach arrays, permanent magnets or a combination thereof. In some embodiments, the electromagnetic field is a rotating field, pulsating field, fixed field, a field comprising a gradient or a combination thereof.

In some embodiments, the signal generator is configured to receive communication messages from the particles. In some embodiments, the communications are via the same signal channel used for other purposes, such as the remote energy transfer channel. Alternatively, the communications are via a separate dedicated channel, including but not limited to electromagnetic, ultrasound, RF, optical or HF channels.

In some embodiments, the imaging module comprises a system selected from an acoustic-based imaging system, an ultrasound-based imaging system, an X-ray-based imaging system, an electromagnetic imaging system, an optics-based imaging system or a combination thereof. In some embodiments, the optics-based system comprises a radio-frequency system. In some embodiments, the imaging module is aimed at visualization of a particle or multiple particles in vitro, ex vivo, in vivo (in an animal) or in a human patient.

In some embodiments, the imaging module may include ultrasound, electromagnetic, optical or alternative elements or a combination thereof, as exemplified by but not limited to ultrasound-computational tomography or any relevant manifestation thereof. In some embodiments, the imaging module is a standalone ultrasound device. In other embodiments, the imaging module comprises multiple ultrasound sensors with integrated tracking logic implemented by the integration module. In some embodiments, the ultrasound device may specifically be configured to visualize the nano- or micro-particles.

In some embodiments, the integration module comprises hardware and software to secure active, pre-determined delivery of particles to specified locations in vitro, in vivo, ex vivo, or in a patient, and accurately control their operation. For example, the integration module contains algorithm logic receiving input from the imaging system to locate particles, communication from particles to ascertain their state and the conditions of their microenvironment, diagnostics from the signal generator module describing electromagnetic field parameters as it pertains to particle control, and input from the delivery and retraction module describing the position of the retraction tool. The integration module, in turn, sends commands to other modules to conduct specific operations, such as: a payload release command to particles at a specific location or timing in tissue, followed by a "change direction of particle motion" command to the signal generator. The signal generator responds to the command by changing the signal to guide particles towards the retraction tool. The imaging system continuously sends tracking data to the integration module, which in turns sends guidance commands to the signal generator to properly guide the particle. When particles reach the retractor, the integration module sends a retraction command to the retraction module, and receives feedback on successful retraction from the retractor.

In some embodiments, the particles are configured to accurately deliver a therapeutic cargo or therapy, or to perform other localized manipulation of the particles or their environment at a specific location and/or at a specific time, as well as to safely and reproducibly retract and collect them from a predetermined location.

In some embodiments, the particles are configured to respond to external stimuli to perform a variety of specialized and localized operations. Examples include: localized thermal ablation by the particle (localized heating), exposure of a radioactive element embedded in the particle, moving of mechanical manipulators on the particle in order to cut surrounding tissue tissue/move it/pierce it, localized vibration of the particle or its components or of surrounding tissue, collection of samples into the particle, pushing or pulling surrounding tissue, unloading other types of cargo from the particle and attaching them to tissue, collecting objects from the particle environment, manipulating other objects (non-tissue) in the particle environment, such as other implantable devices.

In some embodiments, the stimuli comprise signals or remote-control commands transmitted from the external signal generator, signal or commands communicated by other particles, and/or localized chemical or physical stimuli as sensed by particles via embedded sensors.

In some embodiments, the particle may carry specific therapeutic cargo or a combination of several cargos. In some embodiments, the particle may carry diagnostic agents, therapeutic agents or a combination thereof.

In some embodiments, the particles comprise specialized compartments to accommodate: i) adhesion, partial or complete penetration of a tissue; ii) mobility, including complex 3D as well as stop-and-go motion; iii) therapeutic effect, including loading and unloading of specific cargo or a combination of several agents; iv) sample collection from its environment v) uplink and/or downlink communication; vi) sensory; vii) power harvesting; viii) logic control and computation, and/or ix) retraction of particles from operating volume.

In some embodiments, the localized operation may include generating local thermal, electric or radiation exposure. In some embodiments, the localized operation may include neutron particle-based or alpha particle or thermal radiation.

In some embodiments, the localized operation may include manipulation of MEM components connected or embedded in a particle. In some embodiments, the localized operation may include mechanical manipulation of particle environment. In some embodiments, the localized operation may include moving the particle or its components in relation to the environment.

In some embodiments, the localized operation may include partial, complete, spatially and/or temporally determined release of particle cargo. In some embodiments, the particle can actively transport when subjected to the external stimuli. In some embodiments, the particle delivers cargo as a whole, a gradient or in a stop-and-go fashion. In some embodiments, the localized operation may include gathering sensory data, such as medical diagnostics, chemical sensors, flow and/or rheology sensors, temperature, or magnetic field gradient. In some embodiments, the localized operation may include data communication from particles to the external signal generator module or to other particles. In some embodiments, the localized operation may include gathering samples from particle environment, such as a biopsy.

In some embodiments, the particle may exhibit specific features aimed at enhanced imaging and/or detection via external devices. For example, the features may include specialized surface, topology, materials, or a combination thereof. Alternatively, the features may include specialized image enhancing features, as exemplified by microbubbles, localized measurement of magnetic field gradients, or communication antennae.

In some embodiments, particles are embedded with a coil wrapped around a magnetic core to harvest power from a magnetic signal. In some embodiments, particles contain a structural coil as an integral part with a magnetic core insert to harvest power from a magnetic signal.

In some embodiments, the magnetic signal used to power the device has a frequency and/or spatial orientation relative to the device to avoid interference with magnetic signal components used to propel and/or other communicate with the device.

In some embodiments, the delivery and retraction module is configured for pre-determined delivery and collection of particles. In some embodiments, the delivery and retraction module is aimed at controlled delivery and collection of a nano or micro-particle to and from specific locations prior to and after control with external stimuli and upon completion of particle operation. In some embodiments, the delivery and retraction module comprises one or several structural elements aimed at delivery and collection of a particle or a series of particles. In some embodiments, the delivery and retraction module is configured to secure single or multiple insertions for in vitro, ex vivo, in vivo or patient applications. In some embodiments, the delivery and retraction module is configured for single or multiple insertions.

In some embodiments, the delivery and retraction module comprises a magnetic or magnetizable needle for injecting and collection of a particle or a series of particles. In some embodiments, the magnetic or magnetizable needle is configured to accommodate standalone particles or particles in a matrix to secure precise delivery. In some embodiments, the needle may be kept in the injection matrix for the duration of treatment. In some embodiments, the needle may be retracted and reintroduced for particle collection. In some embodiments, the delivery and retraction module comprises alternative delivery techniques based on electromagnetic, ultrasound or pneumatics-based devices. In some embodiments, the delivery and retraction module comprises alternative collection techniques as exemplified by but not limited to deployable mesh, micronet, suction, cutting or a combination thereof.

In some embodiments, the particles comprise a MEM device comprising said integration module, said device comprising:
  at least one cargo container comprising a cavity temporarily sealed by a membrane;
  at least one sensor;
  an electronic circuit; and
  at least one motion element;
  wherein:
    the electronic circuit is configured to control at least one responsive element; and
    the sensor is configured to receive signals transmitted by a remote unit.

In some embodiments, the membrane comprises at least one miniature opening. In some embodiments, the membrane comprises at least one responsive element configured to control cargo release via the membrane. In some embodiments, the responsive element is configured to control cargo release via the membrane or configured to actuate and control motion of the device or a combination thereof.

In some embodiments, the cavity is in the form of a cylinder, a pyramid, a cube, a tube, a ball, a box, a non-symmetric shape, a partially-symmetric shape or a symmetric geometrical shape. In some embodiments, the shape is a basic or distorted shape selected from: cube, tube, ball, box, cylinder, pyramid or a combination thereof. In some embodiments, at least one dimension of the cavity is in the micrometer range or in the nanometer range.

In some embodiments, the motion element comprises a piezoelectric element, a cantilever, a shape-memory element, a membrane, a flagellum, an arm, a joint or a combination thereof.

In some embodiments, the responsive element comprises an elongated element having a first end and a second end. For example, the first end is anchored and the second end is free. Alternatively, both the first and second ends are anchored. In some embodiments, the responsive element is rigid. In other embodiments, the responsive element is flexible.

In another aspect, provided herein are systems, the systems comprise: a platform described herein and a remote unit comprising a transmitter, a receiver or a combination thereof; wherein the remote unit is configured to communicate with the platform. In some embodiments, the transmitter generates an electric field, a magnetic field, an acoustic or ultrasound wave, an electromagnetic wave or a combination thereof. In some embodiments, the receiver receives an electromagnetic signal, an acoustic signal, or a combination thereof.

In another aspect, provided herein are methods for communicating with a MEM device, the methods comprise:
  providing a MEM device comprising:
    at least one responsive element;
    at least one sensor; and
    an electronic circuit;

wherein:
the electronic circuit is configured to control said responsive element; and
the sensor is configured to receive signals transmitted by a remote unit;
transmitting and/or receiving a signal to/from the device, wherein the signal comprises one or more of:
a magnetic signal, an electric signal or a combination thereof;
an acoustic or ultrasound signal;
an electromagnetic radiation signal; or
an optical signal.

In some embodiments, the MEM device has at least one cargo container, comprising a cavity temporarily sealed by a membrane. For example, the device comprises at least one responsive element configured to control cargo release via the membrane or configured to actuate and control motion of the device or a combination thereof. Alternatively, the MEM device has at least one cargo container comprising a cavity containing slow release or other controlled release cargo.

In some embodiments, communicating comprises tracking the location of the device, powering the device, charging the device, propelling the device, directing the motion of the device, triggering an action performed by the device, heating the device or portions thereof, receiving data from the device, controlling the device or a combination thereof. For example, the triggered action comprises releasing payload from a cavity encapsulated in the device.

In some embodiments, the MEM device comprises a cavity, which comprises the responsive element, such that:
the responsive element vibrates in response to an external signal (magnetic/US); and
the vibration powers the IC.

In some embodiments, the cavity is sealed by the responsive element, such that:
the responsive element is in the form of a flexible membrane;
the responsive element vibrates in response to an external signal (magnetic/US); and
the vibration powers the IC.

In some embodiments, the MEM device comprises a cavity, and the responsive element is configured to control its position to an open cavity position or to a sealed cavity position and/or wherein the responsive element triggers motion of the responsive element such that the cavity is opened to release cargo. In some embodiments, following opening of the cavity, the responsive element moves such that the cavity is closed.

In some embodiments, the MEM device comprises a cavity, which comprises a second responsive element that resides within the cavity, such that:
payload is accommodated between the two responsive elements; and
the second responsive element is configured to push/vibrate the payload such that the payload pushes the first (sealing) responsive element to an open cavity position;
whereby payload is released from the cavity.

In some embodiments, the responsive element is in the form of a spring, which stretches in response to a signal generated by the IC (EM/US) such that the payload pushes the first (sealing) responsive element to an open cavity position; whereby payload is released from the cavity, wherein the signal is induced by said IC.

In some embodiments, the first (sealing) responsive element is a valve sealing the cavity and the second responsive element is a driver. For example, the driver is an inkjet, and the second element is a nitinol valve.

In some embodiments, the MEM device comprises a controllable array of heaters connected to separate payload cavities/compartments. Each heater can be turned on separately by the IC to burst a thermo-sensitive membrane and release payload from a specific cavity. This method allows gradual release (rather than all at once).

In some embodiments, the MEM device comprises a cavity, which comprises a second responsive element that resides within the cavity, such that:
payload is accommodated between the two responsive elements and surrounding the second element; and
said responsive element is configured to vibrate such that it stirs said payload;
wherein payload is ejected from the cavity through a perforation in the first (sealing) responsive element.

In some embodiments, the responsive element is anchored to an external surface of the particle, and when the IC vibrates the element, the vibration propels the particle.

In some embodiments, the MEM device comprises a plurality of motion elements, and each of them comprises at least two limbs and at least two joints ($\Theta_i$, $\Phi_i$), and wherein said motion elements are configured to move said device on a surface.

In some embodiments, the signal is an ultrasound signal and the sensor is a flexible vibrating membrane or cantilever located near or in a cavity or an exposed piezoelectric element. In some embodiments, the cavity is filled with a viscoelastic material to match the acoustic impedance of the membrane or cantilever.

In another aspect, provided herein are methods of treating a subject, the methods comprise:
providing a MEM device comprising:
at least one responsive element;
at least one sensor; and
an electronic circuit;
wherein:
the electronic circuit is configured to control the responsive element; and
the sensor is configured to receive signals transmitted by a remote unit;
inserting the device into the subject;
transmitting and/or receiving a signal to/from the device, wherein the signal comprises one or more of:
a magnetic signal, an electric signal or a combination thereof;
an acoustic or ultrasound signal;
an electromagnetic radiation signal; or
an optical signal;
such that said signal is used for a treatment operation on said subject.

In some embodiments, the MEM device comprises a cavity, and the cavity comprises a therapeutic agent, a diagnostics agent, multiple therapeutic and diagnostics agents. In some embodiments, the responsive element is configured to control cargo release via a membrane or configured to actuate and control motion of the MEM device or a combination thereof. In some embodiments, the treatment operation comprises diagnostics, a drug, a combination of thereof or other therapeutic payload release from a cargo container. In some embodiments, the treatment operation is selected from heating/cooling, piercing, dislodging, cutting, scratching, scraping, abrading, marking, binding, applying pressure to, grasping a sample from, mapping, digesting, imaging, releasing therapeutic payload, releasing radioactive material, emitting radiation, exposing radioactive component, or a combination thereof. In some embodiments, the MEM device is inserted into a body area selected from: tissue, blood vessel or vitreous humour.

In some embodiments, therapeutic entities that can be loaded onto the particles or devices, for example into a cavity, described herein comprise at least one of: radionuclides, α-particles and neutron emitters, small molecules, respective prodrugs, peptides, peptoids, antibodies, antibody-drug conjugates, modified antibodies and their derivatives as exemplified but not limited to light chain antibody constructs, nucleic acids as exemplified but not limited to aptamers, antisense oligonucleotides, RNAi, siRNAs, shRNAs, miRNAs.

In some embodiments, the therapeutic payload can comprise components of CRISPR-Cas9 or related gene editing molecules. In some embodiments, the therapeutic payload can include vaccines, such as the Bacillus Calmette-Guerin vaccine. In some embodiments, the therapeutic payload can include oncolytic viruses, such as Talimogene laherparepvec (OncoVEX GM-CSF). In some embodiments, the therapeutic payload can include specialized cells and or cell therapy, such as CART cells or pluripotent stem cells. In some embodiments, the payload can include diagnostics and/or contrasting agents, such as radio-, MRI- or ultrasound contrast agents. In some embodiments, cargo or payload can be loaded in the particle and devices as solids, solutions or alternative formulations, including gels, sols, suspensions, nano- or microformulations, such as micelles, liposomes, mesoporous silica-, carbon nanotube-mediated carriers their composites or alternative particles that supply the intended payload or cargo and fits in a particle or device described herein.

The term "prodrug" refers to a compound that may be converted under physiological conditions or by solvolysis to a biologically active compound. Thus, the term "prodrug" refers to a precursor of a biologically active compound that is pharmaceutically acceptable. In some aspects, a prodrug is inactive when administered to a subject but in vivo is converted to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein. The term "prodrug" is also meant to include covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to a group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

A pharmaceutical composition for the particle may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose.

Agents described herein may be used alone or in combination with appropriate additives to make powders, granules and if desired, with diluents, buffering agents, moistening agents, preservatives, contrasting and diagnostic agents. The compounds or agents may be formulated into the particle with a buffering agent to provide for protection of the compound from external factors. In some cases, the compounds in the particle of this disclosure may be solubilized and encapsulated (e.g., in a liposome or a biodegradable polymer), or used in the form of microcrystals coated with an appropriate nontoxic lipid.

A pharmaceutical composition comprising any one of the compounds or agents to be loaded onto a particle described herein may be formulated for sustained or slow release (also called timed release or controlled release). Such compositions may generally be prepared using well known technology. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. Non-limiting examples of excipients include water, alcohol, glycerol, chitosan, alginate, chondroitin, Vitamin E, mineral oil, and dimethyl sulfoxide (DMSO). The amount of compound contained within a sustained release formulation depends upon the site of treatment, the rate and expected duration of release, and the nature of the condition, disease or disorder to be treated or prevented.

The term "pharmaceutically acceptable carrier" or "pharmaceutically acceptable excipient" includes any and all solvents, dispersion media, coatings, antibacterial and antifungal agents, isotonic and absorption delaying agents and the like suitable for loading into the particle described therein along with therapeutic agent. The use of such media and agents for pharmaceutically active substances is well known in the art. Except insofar as any conventional media or agent is incompatible with the active ingredient, its use in the therapeutic compositions of the disclosure is contemplated. Supplementary active ingredients can also be incorporated into the compositions.

The term "pharmaceutically acceptable excipient" is intended to include vehicles and carriers immobilized onto a said particle and capable of being co-administered with a compound to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with the multi-binding compounds also falls within the scope of the present disclosure.

In making the compositions of this disclosure suitable for loading onto the particle described herein, the active ingredient can be diluted by an excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after particle delivery and payload release to the patient by employing procedures known in the art.

In some cases, pharmaceutical compositions described herein comprise an excipient that provides long term preservation, bulks up a formulation that contains potent active ingredients, facilitates drug absorption, reduces viscosity, adds flavoring, or enhances solubility of the pharmaceutical composition locally in the treated compartment. Non-limiting examples of excipients include anti-adherents, binders (e.g., sucrose, lactose, starches, cellulose, gelatin, or polyethylene glycol), coatings (e.g., gelatin or hydroxypropyl methylcellulose), disintegrants, dyes, flavors (e.g., mint, peach, raspberry, or vanilla), glidants, lubricants, preservatives (e.g., acids, esters, phenols, mercurial compounds, or ammonium compounds), sorbents, or vehicles (e.g., petroleum or mineral oil).

The pharmaceutical compositions disclosed herein may be any type of formulation including solid formulations. In some cases, the liquid formulation may comprise a concentration of active agent. In some cases, a pharmaceutical composition or formulation described herein may comprise a combination of different agents. In some cases, a pharmaceutical composition described herein may comprise at least 2 agents, at least 3 agents, at least 4 agents, at least 5 agents, or more agents.

The active agents loaded onto the particle of the present disclosure, or their pharmaceutically acceptable salts, are generally administered in a therapeutically effective amount. The term "therapeutically effective amount" may generally refer to the amount (or dose) of an agent or other therapy that is minimally sufficient to prevent, reduce, treat or eliminate a condition, or risk thereof, when administered to a subject in need of such agent or other therapy. In some instances, the term "therapeutically effective amount" may refer to that amount of agent or other therapy that is sufficient to have a prophylactic effect when administered to a subject. The therapeutically effective amount may vary; for example, it may vary depending upon the subject's condition, the weight and age of the subject, the severity of the disease condition, the manner of administration and the like, all of which may be determined by one of ordinary skill in the art. The amount of the agent actually administered may be determined by a physician or caregiver, in the light of the relevant circumstances, including the condition to be treated, the chosen route of administration, the agent administered and its relative activity, the age, weight, the response of the individual patient, the severity of the patient's symptoms, and the like.

The active agents loaded onto the particle described herein may be administered to a patient for one or more days. In some cases, the particle could be modulated to make sure the agent is administered to a patient for one day. In some cases, the pharmaceutical composition may be released in controlled fashion to treat the patient for at least 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 20 years, 30 years, 40 years, or 50 years.

The active agents loaded onto the particle described herein may be effective over time. In some cases, the agents are effective for one or more days. In some cases, the duration of efficacy of the agents is over a long time period. In some cases, the efficacy of the agent is greater than 2 days, 3 days, 4 days, 5 days, 6 days, 1 week, 2 weeks, 3 weeks or 1 month.

In some embodiments, more than one agent could be loaded on the particle of the current disclosure and administered at a time to a subject. In some embodiments, two agents of the current disclosure in combination make act synergistically or additively, and either agent may be used in a lesser amount than if administered alone.

Any of the agents could be loaded onto the particle described in combination with a cell therapy and administered to a subject. The effects of the combination may be additive; in some cases, the effects of the combination are synergistic. The agents may be administered before, during or after the administration of the cell therapy. In some cases, the agents are administered separately from the cell therapy. In some cases, the cell therapy is mixed with one or more of the agents.

In some embodiments, the signal is a magnetic signal and the sensor is a micro Hall effect sensor embedded in the device. In some embodiments, the magnetic signal is modulated in a frequency and/or spatial orientation relative to the device to avoid interference with magnetic signal components used for propulsion of and/or remote power transfer to the device.

In some embodiments, the responsive element for controlled cargo release is a membrane, said membrane encloses said cargo container such that said enclosure can assume a closed or an open position, and wherein said membrane is opened and optionally closed in response to an IC signal, such that cargo can be released from said cargo container. In some embodiments, the responsive element for controlled cargo release is placed at least partially within said cargo container, said responsive element can assume a rested or an active position, and wherein said responsive element is activated in response to a remote signal, such that said responsive element pushes cargo within said cavity, such that said cargo is released from said cargo container.

Example 1: Method to Remotely Power or Communicate with Particle/Implantable Devices Using an Electromagnetic Inductive Mechanism Several methods for powering miniaturized medical devices are known (e.g., internal battery, RF-based wireless power transfer, harvesting of biological fuel material available in the body). See, e.g., Basar, et al., *International Journal of Antennas and Propagation*, Volume 2012 (2012); and RF power harvesting: a review on designing methodologies and applications, Tran et al., *Micro and Nano Systems Letters* (2017) 5:14. However, these methods suffer from various limitations, such as:

Internal batteries are greatly limited in storage capacity, especially at the sub-mm scale.

The clinical safety requirements greatly limit choice of materials in battery design.

The efficiency of harvesting biologically available materials in the body as fuels is greatly limited.

Given the approximate scale similarity between RF antenna size and wavelength, constructing an RF receiver antenna at the sub-mm scale requires using the GHz-THz wavelength range, where RF radiation has limited penetration in human tissue. This greatly limits wireless RF power transfer at the sub-mm size scale. For the same reason, RF communication to particles and implantable devices in the human body is challenging to implement on the sub-mm scale, both for the downlink (communication to the particle/implantable device) and for the uplink (transmission from the particle/implantable device).

At the same time, remote inductive charging in the KHz-MHz range is a feasible, efficient option (See, e.g., Carta, et al., *Biosensors and Bioelectronics* 25 (2009) 845-851; Carta, et al., *Sensors and Actuators* A 162 (2010) 177-183). In this method, an external set of Helmholtz coils is located outside the persons body. When an alternating current is present in the coils, it generates an alternating magnetic field through the body. The particle or device in the body contains a miniature 3-Dimensional solenoid S1, wound around a magnetic core based on magnetic material M1. The change in magnetic flux through the solenoid S1 generates current in the solenoid, thereby transferring power wirelessly to the IC (integrated circuit) connected to this solenoid. See FIG. 1. Manufacturing of the solenoid and other IC components on the sub-mm scale is readily available using standard MEM techniques. See, e.g., Le, et al., *Sensors and Actuators A: Physical*, Volume 135, Issue 2, 15 Apr. 2007, Pages 547-551.

However, if a particle which relies on an external rotating electromagnetic field for propulsion (see, e.g., U.S. Pat. No. 8,768,501) is used, the two external magnetic fields (for remote power transfer and for propulsion) may interfere with each other. Specifically, in this case the particle has a separate embedded magnetic component M2 (in addition to the magnetic component M1 described above), which rotates together with the external rotating magnetic field. Thus, it is desirable to ensure that the magnetic field component for remote power transfer does not change the speed or direction of particle motion in a meaningful way.

One solution is as follow:

The total external magnetic field is:

$$B = B1 + B2, \quad \text{Eq. 1}$$

where:
  B1 is a propulsion component (fixed amplitude), whose amplitude is chosen according to the biological medium rheology and particle characteristics to allow sufficient propulsion. Typical values range between 0.01 and 3 T. B never drops below B1; and
  B2 is a power transfer component (varying amplitude)= $C2 + C2*(\cos(wt))$. C2 is chosen to allow sufficient power transfer to the particle (typically below 5 T), and w is the frequency of the remote power transfer field (typically in the Khz-MHz range). B2 ranges between 0 and 2*C2 (never negative);
  both B1 and B2 vectors are in the same direction.

Since the vectors B1, B2 are pointing in the same direction, rotation of the particle follows the direction of B1, irrespective of the magnitude of B2. Furthermore, since the magnitude of B never falls below B1, the external magnetic field is always strong enough to generate sufficient rotation of the particle. Also, the ferri/ferromagnetic material M1 serves the dual function of enhancing the power transferred to the IC through the field component B2, as well as increasing the magnetic moment of the particle, thereby increasing the torque exerted on the particle by the rotating field B1 and generating efficient propulsion.

This method can also be used to create a downlink communication channel to the particle from an external source outside the body using an alternating electromagnetic field (induction). This can be done in 2 ways:

Generating a combined electromagnetic field $B2 = C2(1+\cos(wt)) + C3$, where C2, w are as described above and C3 is a data transfer component at a carrier frequency w2. The values for w and w2 can be chosen to be sufficiently different, and to incorporate in the IC (integrated circuit) a bandpass filtering component to remove signal components except for the frequency w2. Using a single data transfer frequency w2 with modulation of the amplitude yields AM data transfer. This method can be extrapolated to have multiple data transfer frequencies w2, w3, w4, . . . thereby allowing digital FM data transfer. This method is economical in terms of space as it only uses a single solenoid S1 both for downlink data communication and for power transfer. However, it may involve more elaborate IC design including signal filtering components.

Creating 2 separate solenoids S1, S2, connected to 2 RLC circuits with 2 different resonance frequencies w, w2. The first solenoid is used to power the IC and the second is used as downlink communication input to the IC.

Figure 6:
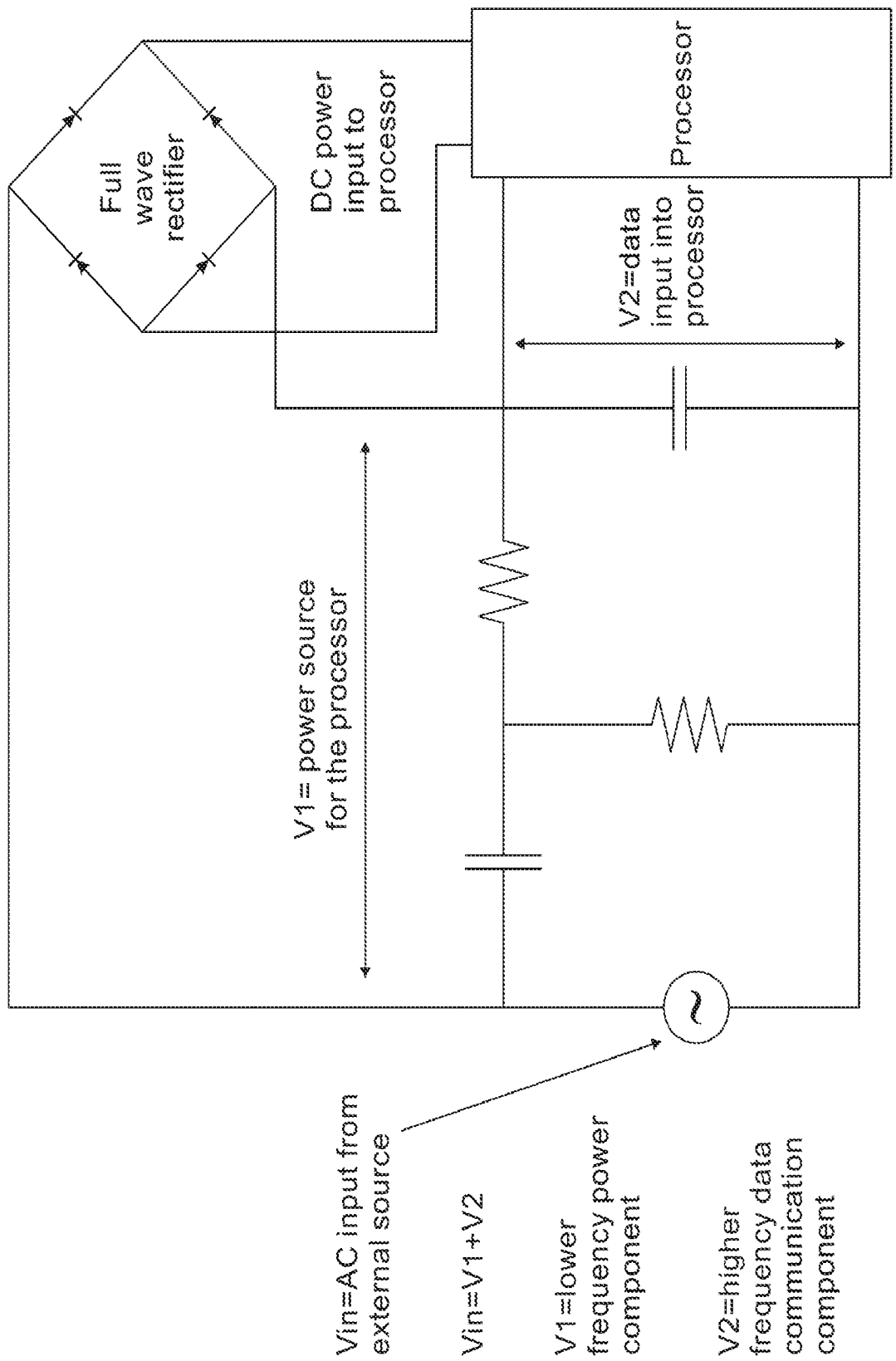
FIG. 6 schematically shows an example of an RLC circuit to split an AC input signal from an external source into two components (a data communication component and a power component) using a band pass filter.

FIG. 6 shows an example of a RLC circuit splitting the signal into two components using a bandpass filter: an AC data communication component fed into the processor and an AC power component (converted to DC before powering the processor). In FIG. 6, the Vin input voltage source represents the embedded solenoid described above (as it generates voltage due to the change in magnetic flux through the solenoid). The same construct can be extrapolated to include multiple bandpass filters on the same circuit, allowing FM data transfer as described above.

Both of these methods of creating the communication downlink circumvent the RF antenna size problems described above. These methods also allow remote powering or communication to a specific object/particle (out of many), by means of selecting an object-specific resonance frequency for the remote energy transfer or downlink communication.

Figure 10:
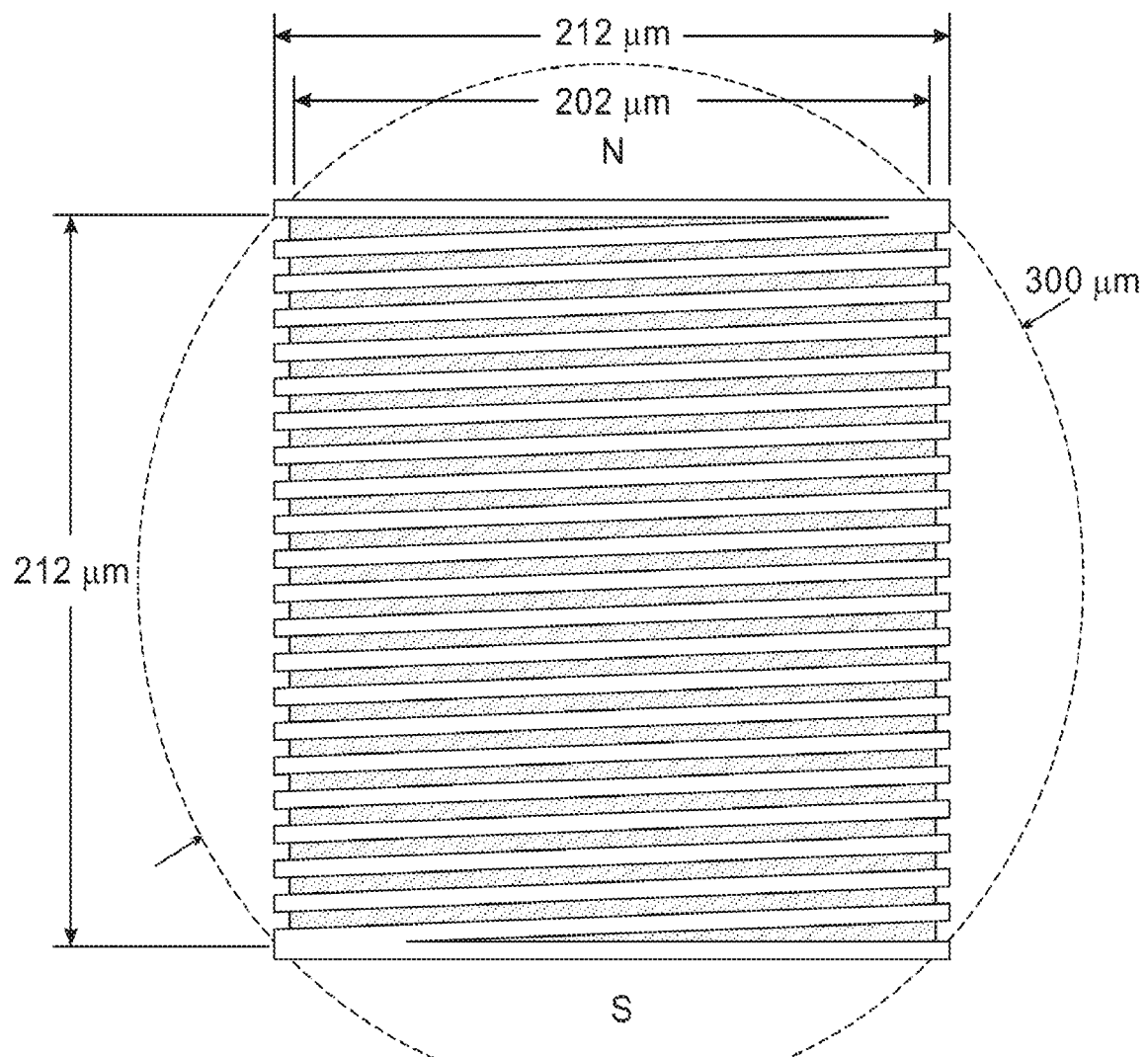
FIG. 10 schematically shows a remote power-harvesting module with a micro-coil wrapped around a magnetic core.

In some embodiments, remote power harvesting by internal device can be done with a micro-coil wrapped around a magnetic core that is embedded in the particle or device, as shown in FIG. 10. The magnetic coil twisted around a core can be manufactured using the following representative method, starting from un-poled neodymium magnet material:

Coat it with an insulator on walls and ends.
  Plate metal on top of the insulator walls and ends
  Use FIB to machine a coil out of the plated metal layer, e.g., with 5 µm lines and spaces.
  Pole the magnet at the end (magnetize it), as placing a magnet in an ion beam is problematic.

Interference between the magnetic signal to the power harvesting coil and the magnetic signal sent to other internal device components (e.g., rotating field for propulsion of internal device, magnetic signal for communication) can be prevented. This can be done by using different frequency bands, filtering specific frequency bands by RLC components embedded in the device, and using different modulation vectors in space (e.g., placing the power harvesting coil symmetry axis orthogonally to the plane of magnetic field rotation, if there is a rotating magnetic field component needed for propulsion—see FIG. 9B).

Figure 12:
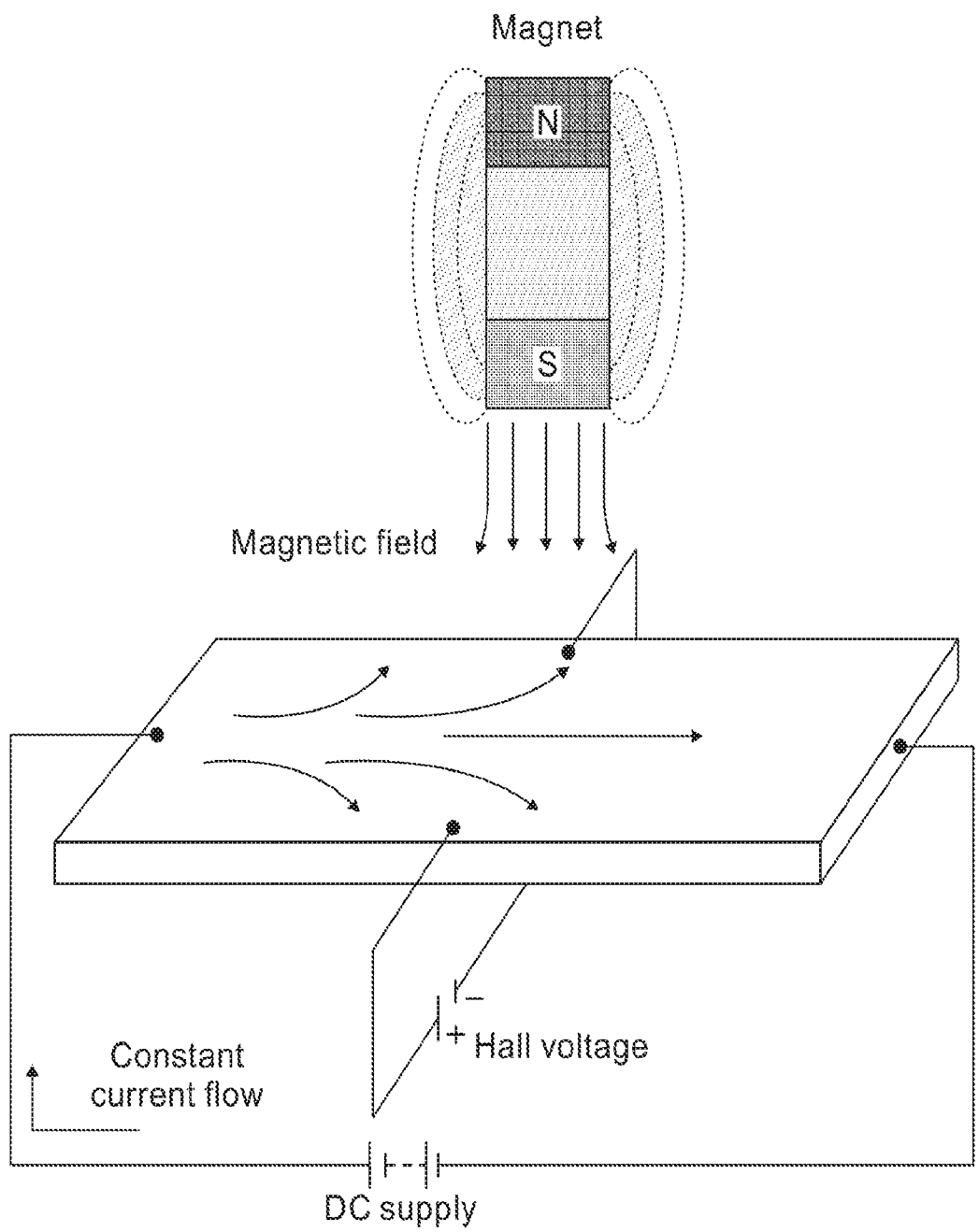
FIG. 12 schematically shows an embodiment where communication with a particle/implantable device is done using a modulated magnetic signal (transmitted by a signal generator) that is picked up by a micro Hall effect sensor embedded in the device.

In some embodiments, communication with the particle or device can be done utilizing a modulated magnetic signal (transmitted by the external signal generator) that is picked up by a micro Hall effect sensor embedded in the particle or device, as illustrated in FIG. 12. The magnetic signal can be modulated in a particular frequency and spatial orientation in relation to the particle or device, to avoid interference with other magnetic signal components, such as signal components used for remote propulsion of said internal device (e.g., rotating magnetic field) and remote power transfer to said internal device. For example, by modulating communication signal in an orthogonal axis to rotation plane of device and at a different, higher frequency (e.g., MHz instead of Hz range), rotation would not be impacted. Similarly, even if the power transfer signal is in same plane as communication signal, the two can occupy different frequency bands (e.g. MHz vs. GHz), avoiding efficient filtering of signal by RLC circuitry embedded in internal device.

Example 2: Method to Remotely Power or Communicate with Particle/Implantable Device Using Ultrasound (US)

Figure 2A:
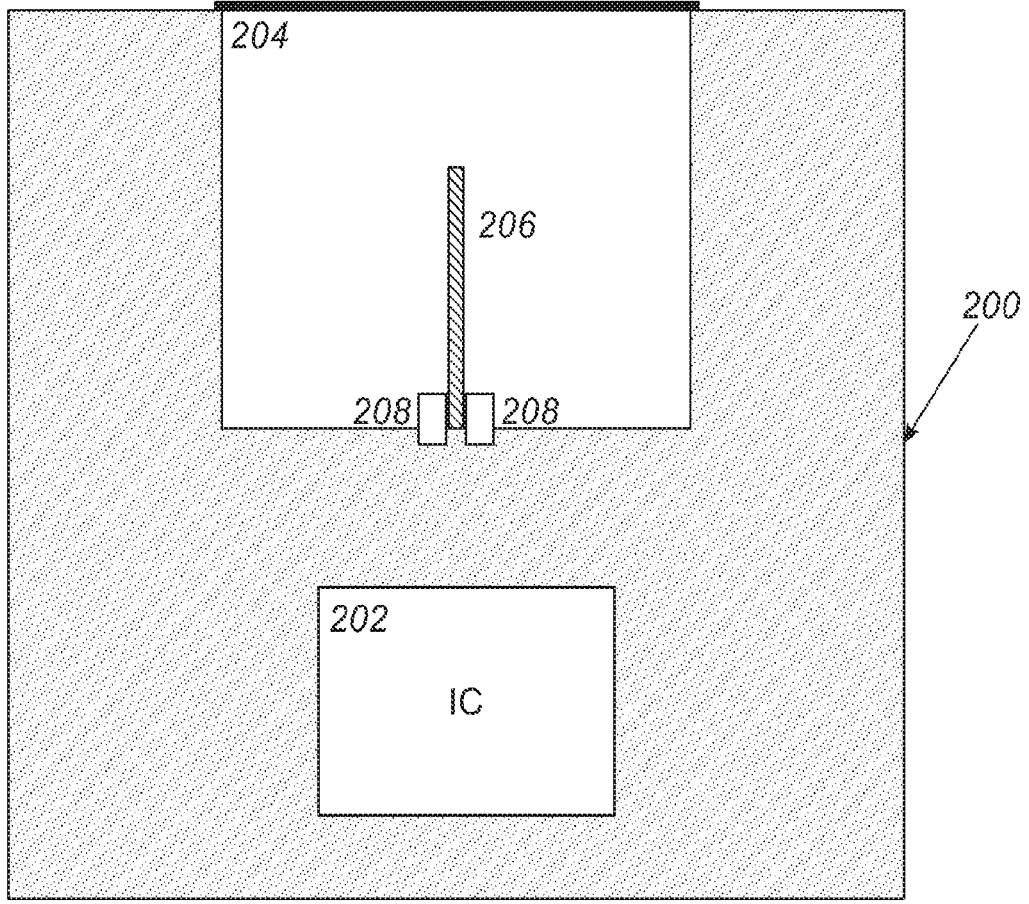
FIG. 2 illustrates cross-sections of: (A) a particle/implantable device 200, the particle comprises a cavity 204, and an embedded IC 202 connected to piezoelectric elements 208. The piezoelectric elements are at the base of flexible cantilever 206. In the absence of an ultrasound signal the flexible cantilever 206 is located inside the cavity 204 in a stationary position; (B) Particle/implantable device 200 as in (A), wherein the flexible cantilever 206 inside the cavity 204 vibrates in response to an external ultrasound (US) signal at resonant frequency. The embedded IC 202 is powered by the piezoelectric elements 208 due to stress generated by the vibrating cantilever 206.
Figure 2B:
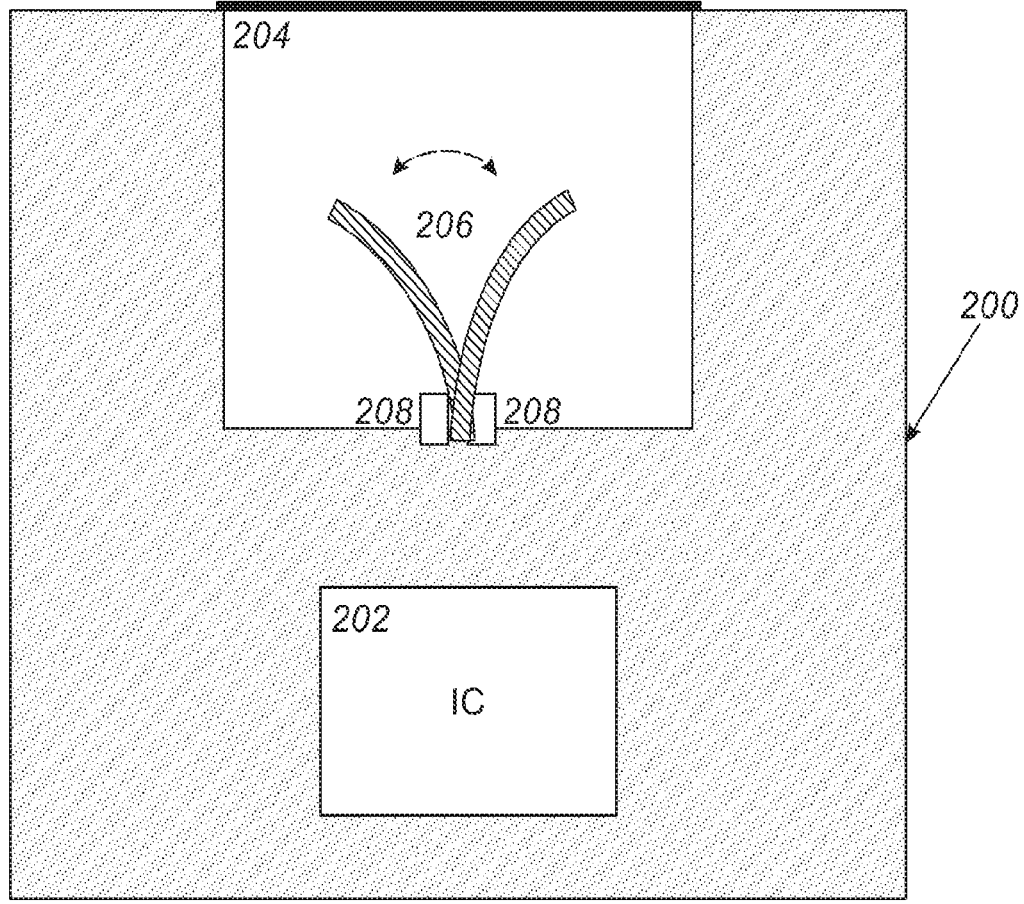

A particle or implantable device can be designed containing one or more flexible elements (e.g., a cantilever, a membrane), with a mechanical resonance frequency X in the KHz-MHz range. The selection of frequency X may be based on the clinical requirements (e.g., existing US equipment to be used, desired penetration depth of the target organ, allowable invasiveness of the procedure). The particle/device size can be in the 100's of nm to cm range. The mechanical resonance frequency of the flexible element can be designed to be X by appropriate choice of the element geometry and material. Multiple options for the design of the flexible mechanical element and the carrier are possible. For example:

A flexible cantilever located inside a cavity: FIGS. 2A and 2B show a particle/implantable device 200, the particle comprises a cavity 204, and an embedded IC 202 connected to piezoelectric elements 208. The piezoelectric elements 208 are at the base of flexible cantilever 206. Cantilever 206 is connected to piezoelectric elements 208, which are in turn connected to IC (integrated circuit) 202 as a power source. When no ultrasound signal at frequency X is present, cantilever 206 does not vibrate significantly (FIG. 2A), and thus does not generate significant mechanical stress in piezoelectric elements 208, which in turn does not generate meaningful voltage. When an external ultrasound signal of frequency X is activated through tissue where the particle is located, cantilever 206 starts vibrating at the resonance frequency (FIG. 2B), and significantly increases the mechanical stress on piezoelectric elements 208 at its base, which in turn generates voltage powering IC 202.

Figure 3A:
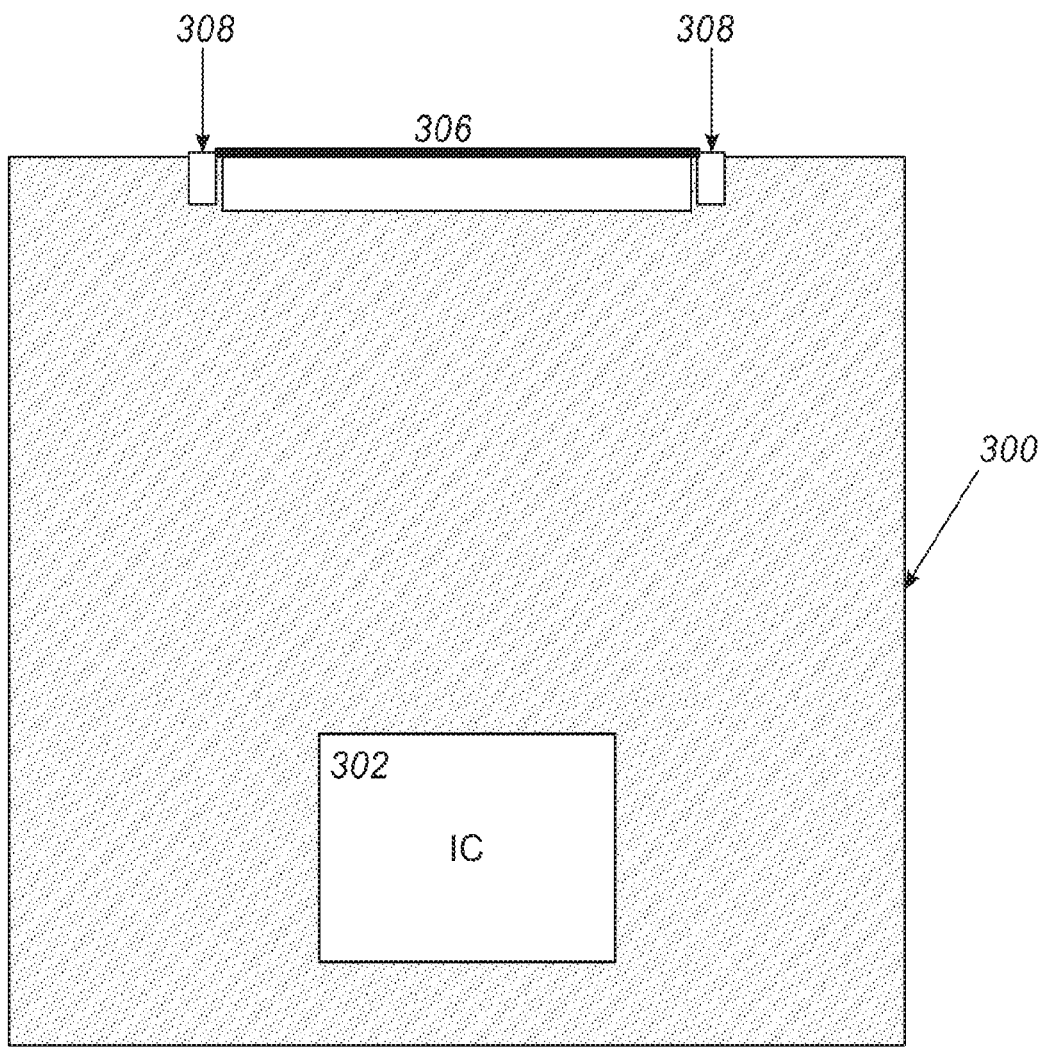
FIG. 3 illustrates cross-sections of: (A) a particle/implantable device 300, the particle comprises an embedded IC 302 connected to piezoelectric elements 308, the piezoelectric elements are at the edges of a flexible membrane 306; (B) Particle/implantable device 300 as in (A), wherein the flexible membrane 306 vibrates in response to external ultrasound (US) signal at resonant frequency. The embedded IC 302 is powered by the piezoelectric elements 308 due to stress generated by the vibrating membrane 306.
Figure 3B:
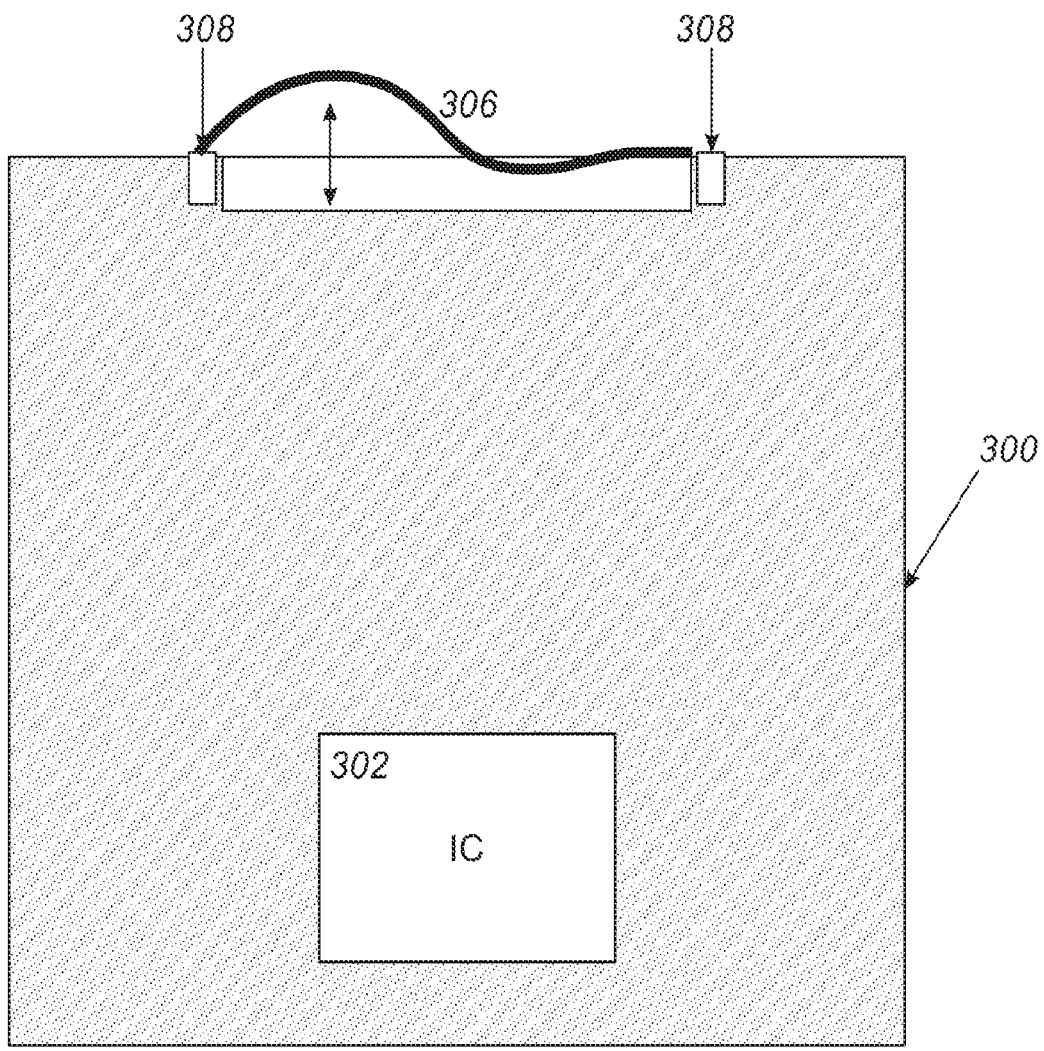

A planar sheet connected to opposing cavity walls: Instead of a cantilever, a different flexible element geometry can be chosen, such as a planar sheet/membrane connected to opposing cavity walls. FIG. 3A illustrates a particle/implantable device 300, when no ultrasound signal at frequency X is present. The particle 300 comprises an embedded IC 302 connected to piezoelectric elements 308 at the edges of a flexible membrane 306. Because no ultrasound signal at frequency X is present, flexible membrane 306 does not vibrate significantly, and thus does not generate significant mechanical stress in piezoelectric elements 308, which in turn does not generate meaningful voltage. When an external ultrasound signal of frequency X is activated through tissue where the particle is located, as in FIG. 3A, flexible membrane starts vibrating at the resonance frequency. The vibrations of sheet 306 at frequency X trigger distortion of the connected piezoelectric elements 308, powering IC 302.

As in Example 1, an ultrasound signal U can be generated of the form:

$$U = A\cos(xt) + B\cos(w2*t) \qquad \text{Eq. 2}$$

where:
$A\cos(xt)$ is the power transfer component; and
$B\cos(w2*t)$ is the downlink communication component.
The values for the frequencies x and w2 can be chosen to be sufficiently different. By incorporating appropriate electronic band pass filters (See FIG. 6) in the IC, all frequency components other than w2 can be removed, thereby accurately receiving the downlink communication. Using a single communication frequency w2 creates an AM (amplitude modulation) signal. This method can be extended to have communication over more than one frequency (w2, w3, w4 . . . ) using multiple frequency filters in the IC. This allows digital communication using FM (frequency modulation). Alternatively, this can be achieved by using multiple flexible mechanical elements, each with a distinct mechanical resonant frequency (instead of using electronic frequency filters in the IC).

FIG. 6 shows an example of a RLC circuit splitting the signal into two components using a bandpass filter: an AC data communication component fed into the processor and an AC power component (converted to DC before powering the processor). In FIG. 6, the Vin input voltage source represents in this Example the AC voltage generated by the piezoelectric element in response to the US signal, as described above. The same construct can be extrapolated to include multiple bandpass filters on the same circuit, allowing FM data transfer as described above.

Analogously to the description above (but in reverse), the IC can generate an output electronic signal, which generates a fluctuating voltage on a piezoelectric element connected to a flexible membrane (akin to an audio speaker). As the voltage fluctuates, the piezoelectric element undergoes fluctuating mechanical deformation, generating US waves. This would generate an uplink US communication channel, in reverse fashion to the downlink communication channel described above. By this method the particle/implantable device can transmit ultrasound signals to the external environment.

Alternatively, vibration of the flexible membrane can be generated by supplying modulated alternating voltage to an electrostatic micro-actuator (see, e.g., Conrad, et al., *Nature Communications* (2015) 6: 10078), or by an IPMC (ionic polymer-metal composite) (see, e.g., Palmre, et al., *Scientific Reports* 4: 6176), or any other suitable method on the sub-mm scale to convert electricity to mechanical actuation. The latter 2 methods (electrostatic micro-actuator, IPMC), may be more applicable in the sub-mm particle/implantable device scenario than using a piezoelectric element for the uplink due to lower voltage requirements.

The amplitude of the uplink signal will be greatly constrained (since the power used by the particle/implanted device is constrained due to the limitations of the local power source or remote power transfer mechanism, and the US signal further decays as it travels through tissue). This may lower the SNR of this signal dramatically. For this reason, this uplink communication signal may be most useful to communicate over short distances inside the body (before significant signal decay). Alternatively, this uplink signal can be received over larger distances outside the body, but may need a more sensitive array of multiple US receivers outside the body to improve the SNR (See Example 4 below).

One or more flexible mechanical components of different shapes and materials located at different positions can be combined on the particle/implantable device based on the methods described above to achieve an optimal effect. The flexible mechanical component can be made of a variety of flexible materials, such as the polymer PET. Representative methods to manufacture it include but are not limited to template-assisted synthesis as exemplified by direct or vertical laser writing, rolled up methodology, photolithographic etching or spinning techniques.

As a non-limiting example of a PET cantilever, choose the length to be 90 microns, the width and thickness to be 30 microns. With a Young modulus of $2\times10^9/m^2$ and a density of $1.4$ g/cm$^2$, the resonant frequency is approximately 200 KHz (using standard formulas for cantilever mechanical resonance orthogonal to cantilever length dimension). Appropriate adjustments of the geometrical parameters and material choice can change the resonant frequency by a factor of 100 or more, either up or down, easily covering the range of KHz to MHz as needed, which covers the frequency range of typical ultrasound pulses.

The design above enables the individual control of several particles or implantable devices in a single unit volume or region. Each particle/implantable device can have a different resonant frequency, thus allowing individual powering and/or communication with a single particle/implantable device by a specific US signal.

In some embodiments, power transfer to and/or communication with the particle or device uses an ultrasound signal transmitted by the external signal generator. The signal can be received by the particle or device using a flexible vibrating membrane/cantilever near/in a cavity (see FIGS. 2A, 2B, 3A, 3B) or an exposed piezoelectric element. The efficiency of ultrasound vibration pickup by cantilever/membrane near a cavity may be degraded due to poor impedance matching, if the cavity is hollow. If this is a problem, the cavity can be filled with viscoelastic material, allowing more efficient acoustic impedance matching and better vibration of cantilever/membrane.

Example 3: Method to Perform IC (Integrated Circuit)—Controlled Mechanical Manipulation by a Particle/Implantable Device Examples 1 and 2 above describe methods to remotely power or communicate with a particle/implantable device. Regardless of powering method (remote power transfer/local power storage/biological fuel harvesting/other) and regardless of communication method (RF/induction-Storage/US/Human Body Communication/other), specific types of localized mechanical manipulation by the particle/implantable device, controlled by the embedded IC (integrated circuit), may be desired. Specific types of manipulation which may be of interest include:
  triggered release of a payload contained in the particle/implantable device (e.g., drug);
  mechanical motion of an external flagellum attached to the particle, to propel the particle in tissue; and
  crawling motion across a surface using a flexible external arm.

Figure 4A:
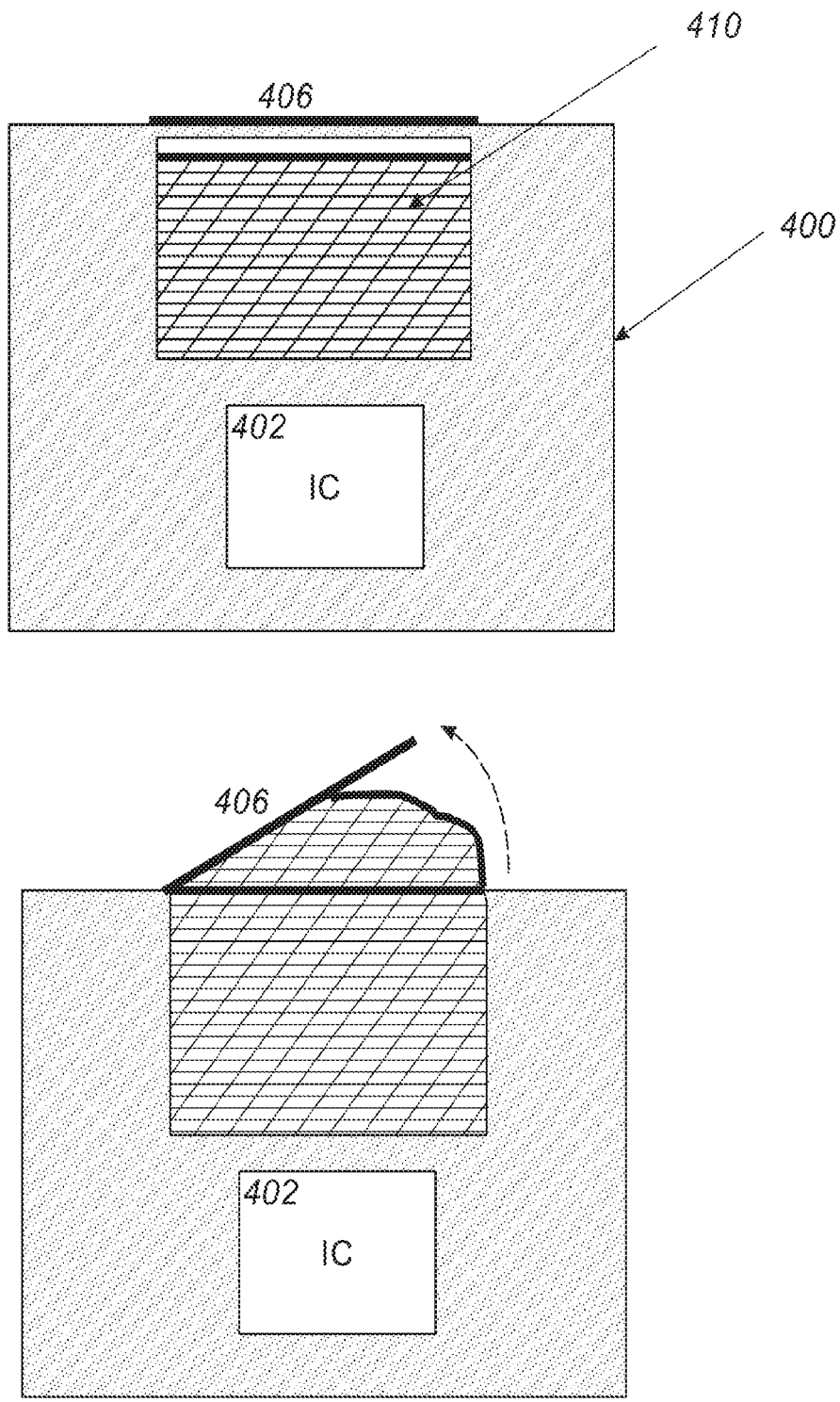
FIG. 4 illustrates cross-sections of: (A) top: a particle/implantable device/carrier 400, carrying a payload 410 encapsulated in a cavity. The particle comprises an embedded IC 402. A membrane 406 connected to an actuator seals the cavity. The actuator is controlled by the IC 402 embedded in the particle/carrier 400; bottom: the actuator opens the seal in response to a signal from the IC 402. The seal opens, allowing the payload to diffuse outside of the cavity; (B) top: a particle/implantable device/carrier 400, carrying a payload 410 encapsulated in a cavity. The particle comprises an embedded IC 402. A first membrane 406 separates the cavity from the environment, with a small opening limiting diffusion. An actuator 412 connected to a second membrane lining the cavity (underneath the payload), is controlled by embedded IC 402. The actuator is controlled by the IC 402 embedded in the particle/carrier; bottom: the actuator 412 pushes the second membrane lining the cavity upward in response to signal from the IC 402 to push the payload 410 out from the cavity; (C) top: a particle/implantable device/carrier 400, carrying a payload 410 encapsulated in a cavity. The particle comprises an embedded IC 402. A membrane 406 separates the cavity from the environment, with a small opening limiting diffusion. An actuator 414, inside the cavity is controlled by embedded IC 402; bottom: the actuator 414 vibrates back and forth in response to signal from the IC, increasing pressure in cavity. Payload is pushed outside from the cavity; (D) a particle/implantable device/carrier 400 comprises an embedded IC 402. An actuator 416 connected to external flexible flagellum vibrates to propel the particle forward; (E) schematics and operation of a crawling particle/device 400 comprising IC 402.

Such types of manipulation can be implemented using methods to convert an electrical signal (the IC output) to mechanical actuation/deformation, on the sub-mm scale, with low voltage requirements. These methods include electrostatic micro-actuators (see, e.g., Conrad, et al., *Nature Communications* (2015) 6: 10078)), IPMC (ionic polymer-metal composites) (see, e.g., Palmre, et al., *Scientific Reports* 4: 6176) or other suitable methods. Given a method to generate mechanical actuation on the micro scale using an electrical signal, the following designs are exemplary implementations:

For example, FIG. 4A illustrates one embodiment of a particle/implantable device/carrier 400, carrying a payload 410 encapsulated in a cavity. The particle 400 comprises an embedded IC 402. A membrane 406 connected to an actuator seals (FIG. 4A, top) the cavity. The actuator is controlled by IC 402 embedded in particle/carrier 400. The actuator bends and opens the seal in response to a signal from the IC 402. The seal opens, allowing the payload to diffuse outside of the cavity (FIG. 4A, bottom).

Figure 4B:
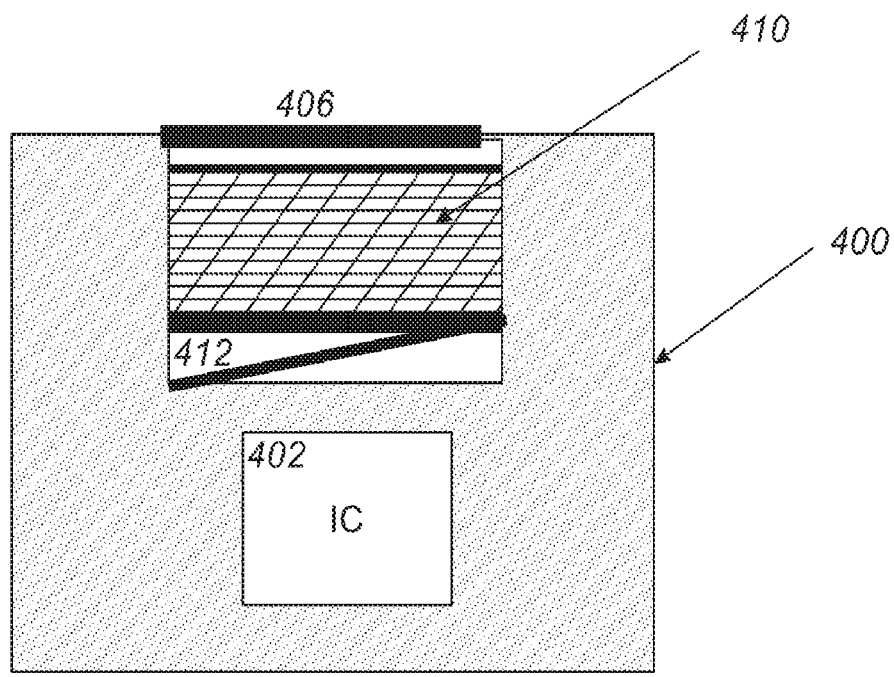
Figure 4B:
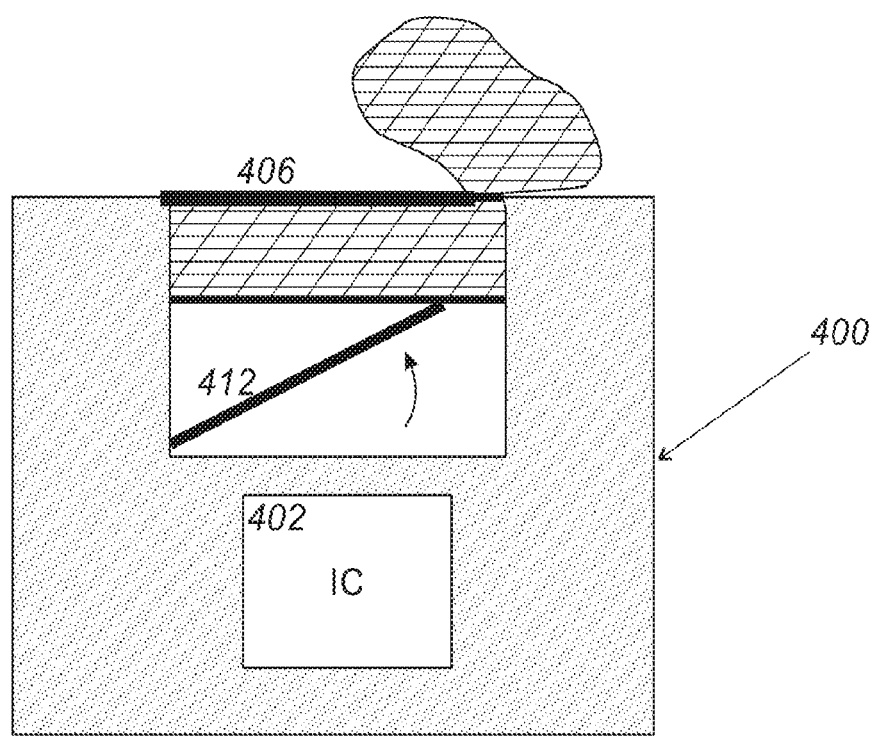

FIG. 4B illustrates another embodiment of a particle/implantable device/carrier 400 with an embedded IC 402, and carrying a payload 410 encapsulated in a cavity. A first membrane 406 separates the cavity from the environment, with a small opening limiting diffusion (FIG. 4B, top). An actuator 412 connected to and below a second membrane lining the cavity (underneath the payload), is controlled by embedded IC 402. The actuator 412 pushes the second membrane lining the cavity upward in response to and electrical signal from the IC 402 to push the payload 410 out from the cavity (FIG. 4B, bottom)

Figure 4C:
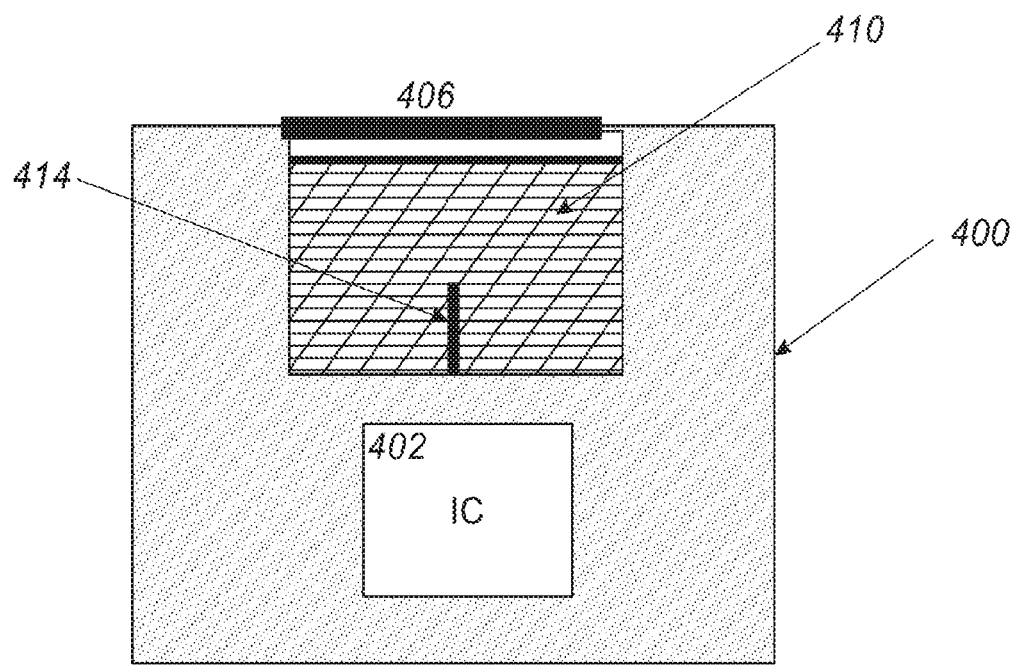
Figure 4C:
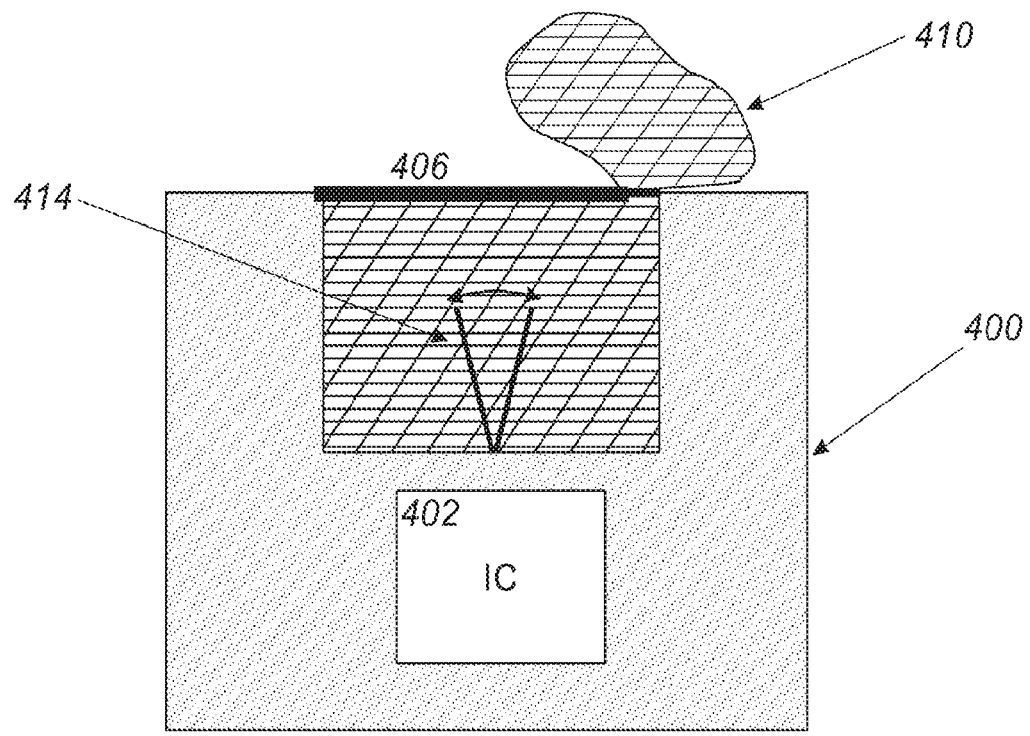

FIG. 4C shows another embodiment of a particle/implantable device/carrier 400 with an embedded IC 402, and carrying a payload 410 encapsulated in a cavity. A membrane 406 separates the cavity from the environment, with a small opening limiting diffusion (FIG. 4C, top). An actuator 414, inside the cavity is controlled by embedded IC 402. Actuator 414 vibrates back and forth in response to signal from the IC, increasing pressure in the cavity. The payload is pushed outside from the cavity as a result (FIG. 4C, bottom).

Figure 4D:
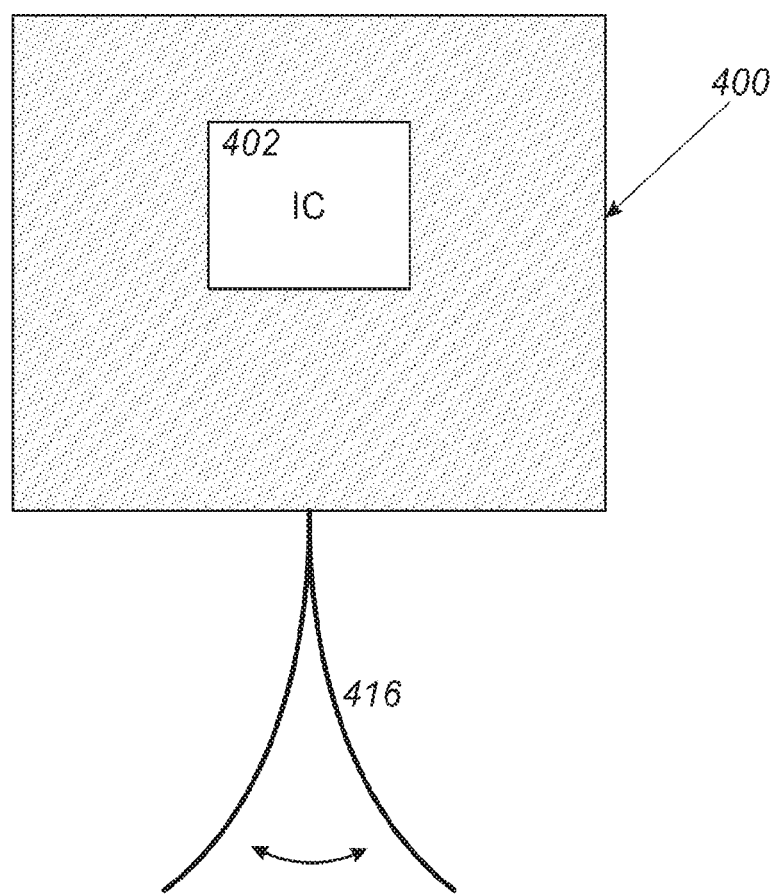

Alternatively, the actuator 416 can be placed outside the particle and linked to a flexible flagellum, as illustrated in FIG. 4D. A fluctuating electrical signal can lead to vibration of the flagellum, propelling the particle forward.

Figure 4E:
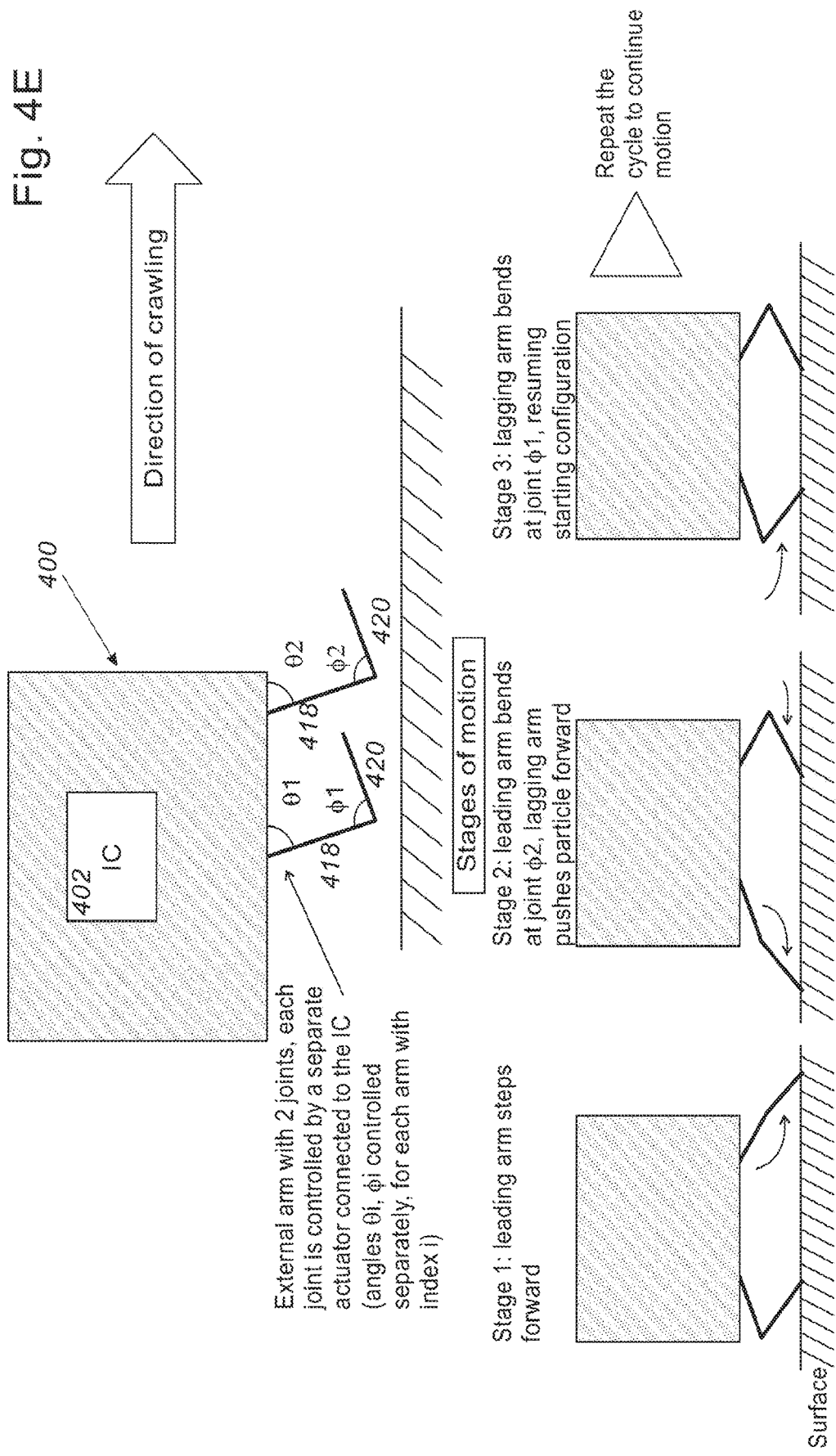

Alternatively, as exemplified in FIG. 4E, one or more flexible crawling arms are connected to the particle on the outside. Several distinct electrical signals control distinct joints of each flexible crawling arm, generating a crawling motion on a surface. The surface on which the particle crawls may be located at any orientation relative to the particle (horizontal/vertical/etc.) and that the crawling arms can be located anywhere on the particle. As exemplified in FIG. 4E, only 2 crawling arms are shown. The total number of crawling arms can be larger than 2, enabling more stable motion and larger torque than possible with just 2 crawling arms. The crawling motion can also be assisted by other mechanisms, such as an externally applied rotating electromagnetic field propelling the particle forward, or a chemical coating or infusion of the particle with a substance which makes the surrounding biological medium more easily penetrable (e.g., coating by a proteolytic enzyme).

Figure 11:
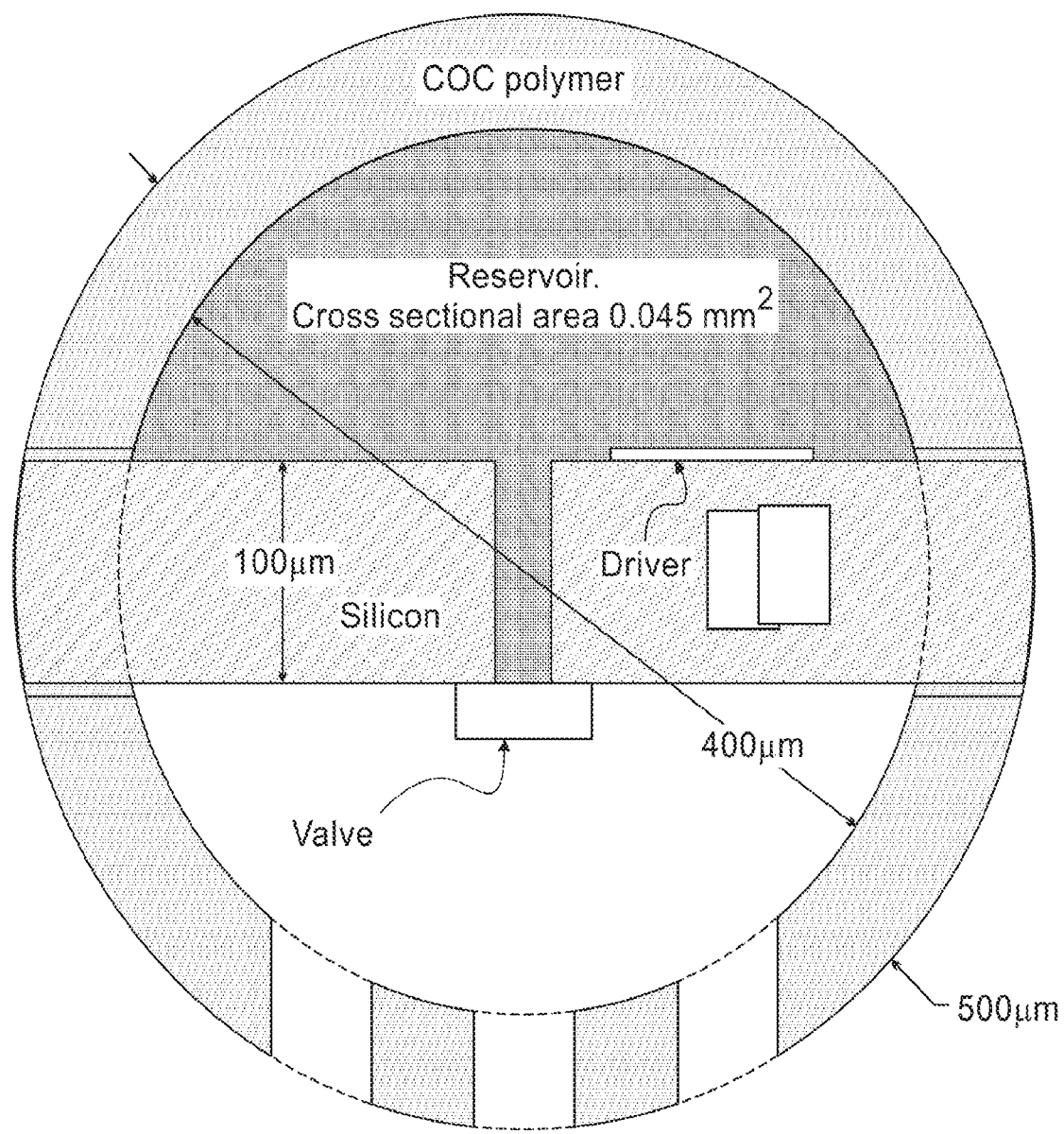
FIG. 11 schematically shows a payload contained in cavity or reservoir within a particle/implantable device. The payload is released using a combination of a driver inside the cavity pushing the payload outside of the cavity thru a valve opening/sealing the cavity.

Another embodiment for triggered release of a payload contained in the particle/implantable device is depicted in FIG. 11. FIG. 11 shows a payload contained in a cavity or reservoir within the particle/implantable device. The payload can be released using a combination of a driver inside the cavity pushing the payload outside of the cavity and a valve opening/sealing the cavity.

Other MEM-controlled configurations to expel a payload from the particle/implantable device in a triggered fashion include, but not limited to, the following:
- Liquid payload with a thermal/piezoelectric inkjet for expulsion plus a check valve to prevent premature leakage.
- Multiple thermal/piezoelectric inkjets for multiple liquid chambers with single-use check valves (allowing gradual controlled release of payload).
- Liquid in pressurized chamber with thermally actuated nitinol valve.
- Melting multiple solid pellets containing payload, one at a time (thermal heater array controlled by IC).
- Drug-laden PLA solid pellets expelled one at a time by nitinol spring.
- An array of heaters can be used to burst microencapsulated payload (where carrier membrane is thermosensitive).

The principles and logic of this Example can be extended to multiple other types of localized mechanical manipulation, including localized surgical operations such as incisions, injections, encapsulation of substance from the environment for analysis, etc.

Example 4: Method to Control Fleet of Multiple Devices/Particles Utilizing Central Control Station Examples 1, 2, and 3 above describe various methods to power particles/implantable devices, to communicate with them (uplink-Pdownlink channels), and to control localized mechanical manipulation by the particles using signals from the embedded IC (integrated circuit). In many clinical scenarios, it may be beneficial to control multiple particles or implantable devices at the same time. For example, multiple devices may be needed to deliver different drugs/therapies at the same moment, or to gather diagnostics in an orchestrated, time-sensitive manner Data may need to be transferred from one particle/implantable device to another (e.g., a localized chemical measurement, a confirmation of drug release).

However, as mentioned above, while reliable downlink communication methods (induction-based, US) are provided, the uplink communication methods are often limited in their SNR, due to the power limitation of the transmitting particle/implantable device, and signal decay in tissue. Such uplink communication systems include US, RF, HBC (Human Body Communication; see U.S. Pat. No. 7,307,544). Accurately decoding the uplink signal, may involve complicated signal processing circuitry to amplify the signal and filter out interferences. While implementing complex signal processing circuitry on the sub-mm scale is challenging due to space constraints, doing so externally outside the body is easier (without space constraints and with great computational power at one's disposal).

Figure 5A:
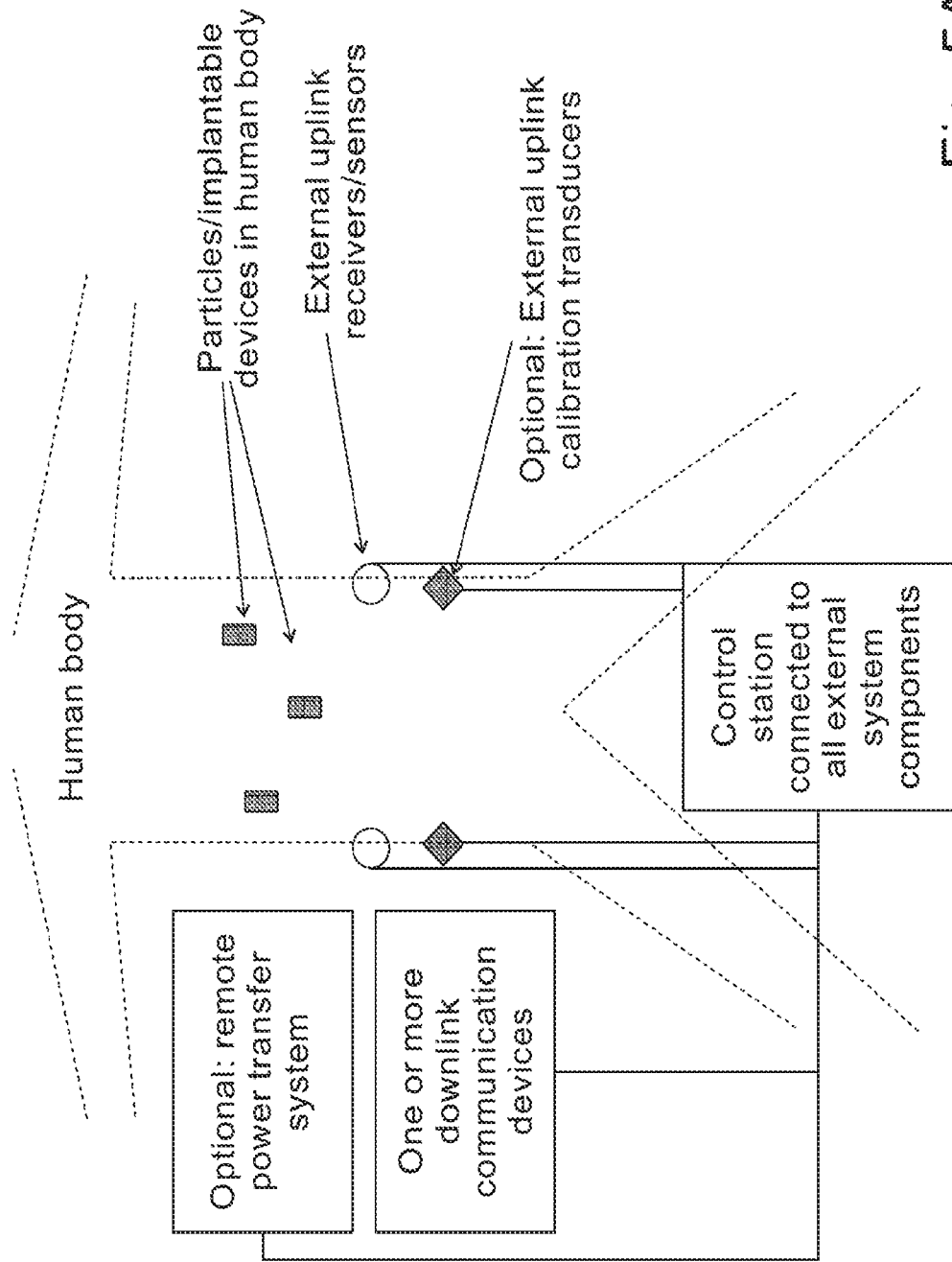
FIG. 5 (A) schematically shows control of particles/implantable devices in a human body; (B) and (C) schematically show communication between particles A and B in a human body. One or more downlink communication devices and multiple uplink receivers/sensors are connected to a centralized control station and placed outside the body.
Figure 5B:
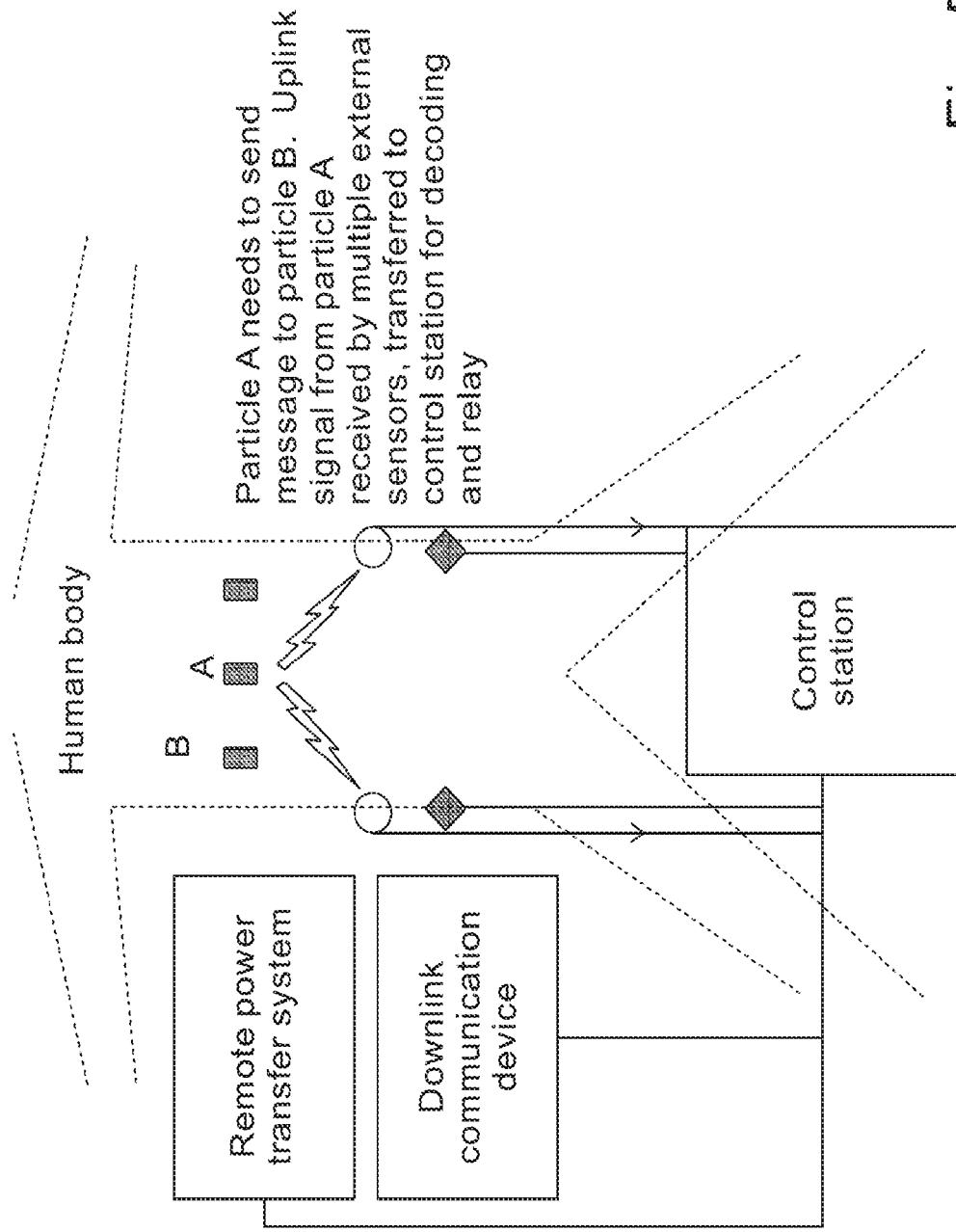
Figure 5C:
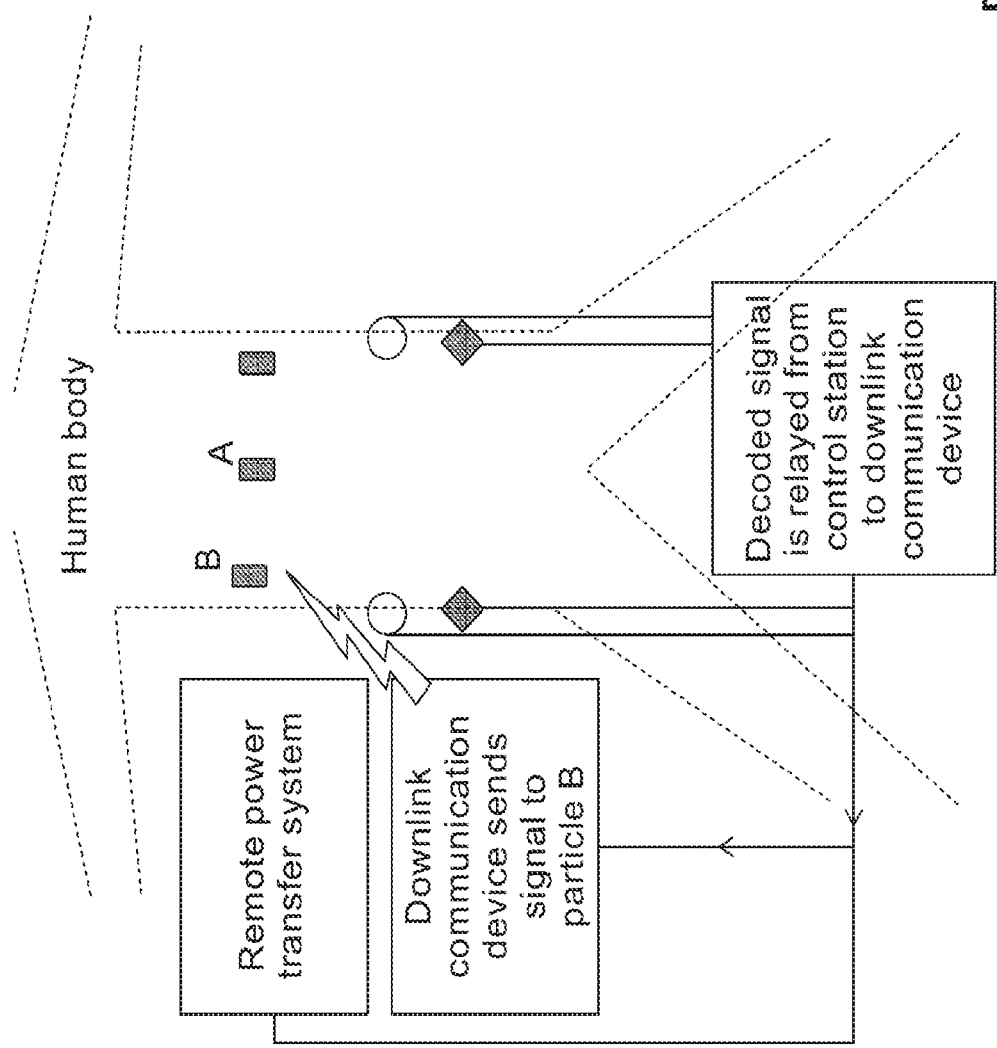

FIGS. 5A-5C show a system design comprising the following components:
- Multiple particles or implantable devices are placed in the body, according to medical requirements. The devices may need to communicate with each other.
- If needed, one or more remote powering devices can be placed outside the body to remotely power the particles/implantable devices.
- One or more downlink communication devices are placed outside of the body, to send signals to particles/implantable devices. The communication devices may be based on magnetic induction, US, or other methods. The communication devices are connected to a centralized control station, which may be a computer or an integrated circuit.
- Multiple uplink receivers or sensors are placed outside the body, to effectively record the uplink channel communication from the particles/implantable devices in the body. The receivers are connected to the control station, which in turn amplifies and filters the uplink signal to accurately decode it.
- If needed, one or more uplink calibration transducers are placed outside the body, allowing the accurate decoding of the uplink channel communication. The calibration transducers utilize the same communication method as the uplink receivers/sensors, which may be US, RF, HBC, or any other applicable method. See below for a decoding procedure for the uplink communication channel.

The downlink communication method does not have to be the same as the uplink communication method.

The control station sends individual commands to the particles/implantable devices as needed and collects their feedback. Whenever data needs to be transferred from one particle or implantable device to another, it is transferred using the uplink communication channel to the centralized control station (FIG. 5B), which is used as a relay. The centralized control station accurately analyzes the uplink channel signal and sends an individualized signal using the downlink channel (FIG. 5C).

This system design is compatible with magnetic particles, which are propelled by a rotating electromagnetic field, and offers an economic design wherein a single system component serves multiple purposes. For example, the rotating electromagnetic field can be generated by a set of Helmholtz, Maxwell coils or a combination thereof located outside the body. The same coils can be used for remote power transfer and downlink communication with the particles. The uplink channel can be implemented using US sensors placed on the skin, or using HBC electrodes on the skin, or other methods.

Analogously, if US is used, it can be utilized for multiple purposes, significantly simplifying system design and lowering cost. For example, US transmitters/receivers placed outside the body can be used for remote powering of the particles/implantable devices, for the tracking of their particle/device location in tissue, and for the downlink and uplink communication with particles/devices.

Procedure to decode the uplink communication channel:

The uplink receivers/sensors and uplink calibration transducers are used to increase SNR of the uplink signal sent from the internal particles/implantable devices. Instead of sending the signals directly from one particle to the other across tissue (with low SNR), the uplink signal is decoded by the external control station, and then relayed back using the downlink to the right particle (with high SNR). Several options can be devised to increase SNR utilizing multiple uplink sensors located outside the body, such as:
- Averaging of the same transmitted signal utilizing multiple sensors. Under an assumption of Gaussian noise, the original signal S is measured at external sensor i as $F(S)+\varepsilon_i$, where $\varepsilon_i \sim N(0,\sigma)$ (i.e., a normally distributed mean zero variable). Assuming F(S) can be decoded using other methods (see examples below), we can average the signal over n sensors, getting the result $$\frac{1}{n}\sum_{i=0}^{n} F(S) + \varepsilon_i = F(S) + \frac{1}{n}\sum_{i=0}^{n} \varepsilon_i \qquad \text{Eq. 3}$$

The noise factor scales inversely with the square root of the number of sensors, i.e., $$\frac{1}{n}\sum_{i=0}^{n}\varepsilon_i \sim N\left(0, \frac{\sigma}{\sqrt{n}}\right) \quad \text{Eq. 4}$$

Hence, using multiple sensors outside the body effectively increases the SNR as much as needed, which is not possible using only a single sensor.

Calculating the frequency response of the body to the transmitted signal, and devising an inverse transformation to decode the signal In the formulation above, F(S) is the transformation applied by the human body on the initial signal S as it travels through the body. In order to decode it, estimate the frequency response or pulse response of the system is needed, and then design the inverse filter F' to accurately decode the signal. Assuming a linear, known frequency response (e.g., change of amplitude and phase), a linear combination of inverse transformations, for different frequencies, can be used to decode the signal. For this purpose, assume Fi is the transformation applied to the component at frequency i. In a simple case, Fi is simply multiplication by a complex number combining phase shift and amplitude change. In that scenario, F can be described as a diagonal matrix with Fi occupying the diagonal). If F is non-singular, we can use F'i=the inverse transformation for each frequency component i can be used, creating the inverse diagonal matrix F'. Hence, the external control station can decode the received signal as F'F(S)=S.

For this procedure, an accurate estimate for the function Fi is needed. As a first step, an external uplink sensor and an external uplink calibration transducer can be located across the relevant body section where the particle/implantable device will eventually be located. The calibration transducer transmits a set of predefined calibration signals across the body at various frequencies (or a continuous frequency sweep). The sensor measuring the response to each calibration signal calculates the corresponding properties of the frequency response (e.g., change in phase, amplitude). Since both transducer and sensor are connected to the control station, they can be coordinated to measure phase and amplitude accurately, and the procedure can be repeated multiple times using different transducer-sensor pairs located across the relevant body area. The resulting frequency response function is then inverted for each frequency Fi, as described above. Finally, the transformation F' as described above is calculated and the signal decoded by the control station. This procedure can be performed without the use of an external calibration transducer. Instead, the calibration signals can be transmitted by the particles/implantable devices in the body and received by the uplink sensors outside the body.

This procedure to estimate F' could be extended to non-linear frequency response functions, using an existing algorithm to estimate the frequency response function and devise a digital inverse function using the control system. For instance, it is possible to use the method described in Lang & Billings, *IEEE Transactions on Circuits and Systems—II: Analog and Digital Signal Processing*, Vol. 47, No. 1, January 2000. Using an external control station allows implementation of such complex signal processing logic at will (which would be challenging if it were implemented in a particle/implantable device inside the body, with size and power constraints).

Furthermore, by analyzing the background signal in the absence of the uplink signal (e.g., the baseline US noise of the human body, the ambient electrical signal generated by surrounding power equipment), it is possible to filter it out using signal processing equipment located outside the body (e.g., a specific bandpass filter). In summary, decoding the received uplink signal by a single particle or implantable device located inside the body is challenging, due to limitations on chip size, power requirements, and computational capacity. However, this becomes feasible by using an external array of sensors connected to a centralized control station with numerical analysis and signal processing capabilities.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A platform comprising the following modules:
   one or more particles, each of said particles having a size between about 100 nm and about 1000 μm and comprising embedded logic and microelectromechanical (MEM) components, each of said particles further comprising a remote power-harvesting component configured to harvest power from ultrasonic signals of a predetermined frequency to power said MEM components thereof;
   a delivery and retraction module configured to deliver and retract said particles;
   an external signal generator;
   an imaging module configured to monitor said particles; and
   an integration module configured to receive inputs from and to provide output control commands to said particles, said delivery and retraction module, said external signal generator and said imaging module;
   wherein:
   said particles, said delivery and retraction module, said external signal generator, said imaging module, and said integration module are configured to interact/communicate with each other; and are controlled internally and/or externally, thereby providing predetermined, fully controlled, precise delivery of said particles in vitro, in vivo, and/or in a patient; and
   the power-harvesting component comprises a flexible element having a resonance frequency which is equal to said predetermined frequency and a piezoelectric element connected to said flexible element.

2. The platform of claim 1, wherein said particles are configured to carry and control release of single or multiple cargo, to perform diagnostics, to perform localized manipulation of their environment, or a combination thereof.

3. The platform of claim 1, wherein said external signal generator is selected from: an electromagnetic signal generator, a combination of a permanent magnet and an electromagnetic signal generator, an optical signal generator, an ultrasound signal generator or a combination thereof.

4. The platform of claim 3, wherein an electromagnetic signal generated by said external signal generator is used to accurately locate said particles by generating a set of distinct electromagnetic features measurable by said particles across operation space and serving as coordinates in operational space.

5. The platform of claim 3, wherein said external signal generator is configured to receive communication messages from said particles.

6. The platform of claim 1, wherein said integration module comprises hardware and software to secure active, pre-determined delivery of said particles to specified locations in vitro, in vivo, ex vivo, or in a patient, and at accurate control of their operation.

7. The platform of claim 1, wherein said particles comprise a MEM device comprising said integration module, said MEM device comprising:
   at least one cargo container comprising a cavity temporarily sealed by a membrane;
   at least one sensor;
   an electronic circuit;
   at least one motion element;
wherein:
   said electronic circuit is configured to control at least one responsive element;
   said at least one sensor is configured to receive signals transmitted by a remote unit.

8. The platform of claim 7, wherein said membrane comprises at least one miniature opening and said at least one responsive element is configured to control cargo release via said membrane.

9. The platform of claim 7, wherein said at least one responsive element is configured to control cargo release via said membrane or is configured to actuate and control motion of said MEM device.

* * * * *